(12) United States Patent
Huang et al.

(10) Patent No.: US 8,512,958 B2
(45) Date of Patent: Aug. 20, 2013

(54) METHODS OF IDENTIFYING AGENTS THAT MODULATE MITOCHONDRIAL FUNCTION

(75) Inventors: Yadong Huang, San Francisco, CA (US); Jens Brodbeck, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 785 days.

(21) Appl. No.: 11/636,110

(22) Filed: Dec. 7, 2006

(65) Prior Publication Data

US 2007/0178535 A1    Aug. 2, 2007

Related U.S. Application Data

(60) Provisional application No. 60/748,661, filed on Dec. 7, 2005.

(51) Int. Cl.
*C12Q 1/68* (2006.01)
*G01N 33/53* (2006.01)

(52) U.S. Cl.
USPC ............................... 435/6.16; 435/7.21

(58) Field of Classification Search
None
See application file for complete search history.

(56) References Cited

U.S. PATENT DOCUMENTS 6,046,381 A    4/2000    Mucke et al.

FOREIGN PATENT DOCUMENTS

WO    WO0019200 A1    4/2000
WO    WO 2007/075318    7/2007

OTHER PUBLICATIONS

Chang, S., et al. Lipid- and receptor-binding regions of apolipoprotein E4 fragments act in concert to cause mitochondrial dysfunction and neurotoxicity. PNAS. 2005, vol. 102, No. 51, pp. 18694-18699.
Edland, S., et al. Mitochondrial genetic variants and Alzheimer disease: A case-control study of the T4336C and G5460A variants. Alzheimer Disease and Associated Disorders. 2002, vol. 16, No. 1, pp. 1-7.
Huang et al., "Apolipoprotein E fragments present in Alzheimer's disease brains induce neurofibrillary tangle-like intracellular inclusions in neurons", PNAS (2001), vol. 98, No. 15, pp. 8838-8843.
Mazur-Kolecka et al., "Apolipoproteins E3 and E4 induce, and transthyretin prevents accumulation of the Alzheimer's beta-amyloid peptide in cultured vascular smooth muscle cells", Brain Research, 698:217-222 (1995).
Brough, David, et al., "Agonist-Induced Regulation of Mitochondrial and Endoplasmic Reticulum Motility", 2005, Biochem. J., vol. 392, pp. 291-297.
De Vos, Kurt J., et al., Expression of Phosphatidylinositol (4,5) Bisphosphate-specific Pleckstrin Homology Domains Alters Direction but Not the Level of Axonal Transport of Mitochondria, 2003, Molecular Biology of the Cell, vol. 14, pp. 3636-3649.
Kalbacova, Marie, et al., "Comparison of the Effect of Mitochondrial Inhibitors on Mitochondrial Membrane Potential in Two Different Cell Lines Using Flow Cytometry and Spectrofluorometry", 2003, Cytometry, Part A, vol. 52A, pp. 110-116.
Loew, Leslie, et al., "Imaging in Five Dimensions:Time-Dependent Membrane Potentials in Individual Mitochondria", 1993, Biophysical Journal, vol. 65, pp. 2396-2407.
Overly, Caroline C., et al. "Organelle motility and metabolism in axons vs dendrites of cultured hippocampal neuron", 1996, Journal of Cell Science, vol. 109, pp. 971-980.
Petit, Patrice X., "Alterations in Mitochondrial Structure and Function Are Early Events of Dexamethasone-induced Thymocyte Apoptosis", 1995, The Journal of Cell Biology, vol. 130, pp. 157-167.
Trushina, Eugenia, et al. "Mutant Huntingtin Impairs Axonal Trafficking in Mammalian Neurons in Vivo and in Vitro", 2004, Molecular and Cellular Biology, vol. 24, No. 18, pp. 8195-8209.
Yi, Muqing, et al., "Control of mitochondrial motility and distribution by the calcium signal: a homeostatic circuit", 2004, The Journal of Cell Biology, vol. 167, No. 4, pp. 661-672.
Hashimoto, et al., "Neuronal apoptosis by apolipoprotein E4 through low-density lipoprotein receptor-related protein and heterotrimeric GTPases", J. Neuroscience (Nov. 2000), 20(22):8401-9408.
Examiner's Report Issued by the Canadian Patent Office on Apr. 22, 2013, 4 pages.

*Primary Examiner* — Robert C Hayes
(74) *Attorney, Agent, or Firm* — Paula A. Borden; Bozicevic, Field & Francis LLP.

(57) ABSTRACT

The present invention provides isolated cells comprising a nucleic acid encoding a toxic form of apoE. The present invention further provides screening methods for identifying compounds that reduce apoE-induced impairment of mitochondrial integrity and/or function. The present invention further provides kits for use in carrying out a subject screening method. The present invention provides agents that reduce apoE-induced impairment of mitochondrial integrity and/or function; and use of such agents in the treatment of apoE-related disorders.

17 Claims, 19 Drawing Sheets

FIG. 6

Human apoE4

Lys Val Glu Gln Ala Val Glu Thr Glu Pro Glu Pro Glu Leu Arg Gln
1                5                    10                   15
Gln Thr Glu Trp Gln Ser Gly Gln Arg Trp Glu Leu Ala Leu Gly Arg
            20                   25                   30
Phe Trp Asp Tyr Leu Arg Trp Val Gln Thr Leu Ser Glu Gln Val Gln
        35                   40                   45
Glu Glu Leu Leu Ser Ser Gln Val Thr Gln Glu Leu Arg Ala Leu Met
    50                   55                   60
Asp Glu Thr Met Lys Glu Leu Lys Ala Tyr Lys Ser Glu Leu Glu Glu
65                   70                   75                   80
Gln Leu Thr Pro Val Ala Glu Glu Thr Arg Ala Arg Leu Ser Lys Glu
                85                   90                   95
Leu Gln Ala Ala Gln Ala Arg Leu Gly Ala Asp Met Glu Asp Val Cys
            100                  105                  110
Gly Arg Leu Val Gln Tyr Arg Gly Glu Val Gln Ala Met Leu Gly Gln
            115                  120                  125
Ser Thr Glu Glu Leu Arg Val Arg Leu Ala Ser His Leu Arg Lys Leu
    130                  135                  140
Arg Lys Arg Leu Leu Arg Asp Ala Asp Asp Leu Gln Lys Arg Leu Ala
145                  150                  155                  160
Val Tyr Gln Ala Gly Ala Arg Glu Gly Ala Glu Arg Gly Leu Ser Ala
                165                  170                  175
Ile Arg Glu Arg Leu Gly Pro Leu Val Glu Gln Gly Arg Val Arg Ala
            180                  185                  190
Ala Thr Val Gly Ser Leu Ala Gly Gln Pro Leu Gln Glu Arg Ala Gln
            195                  200                  205
Ala Trp Gly Glu Arg Leu Arg Ala Arg Met Glu Glu Met Gly Ser Arg
    210                  215                  220
Thr Arg Asp Arg Leu Asp Glu Val Lys Glu Gln Val Ala Glu Val Arg
225                  230                  235                  240
Ala Lys Leu Glu Glu Gln Ala Gln Gln Ile Arg Leu Gln Ala Glu Ala
                245                  250                  255
Phe Gln Ala Arg Leu Lys Ser Trp Phe Glu Pro Leu Val Glu Asp Met
            260                  265                  270
Gln Arg Gln Trp Ala Gly Leu Val Glu Lys Val Gln Ala Ala Val Gly
    275                  280                  285
Thr Ser Ala Ala Pro Val Pro Ser Asp Asn His    (SEQ ID NO:1)
290                  295

FIG. 7A

```
HU      KVEQAVETEPEPELRQQTEWQSGQRWELALGRFWDYLRWVQTLSEQVQEE  50
Ba             P  P     DV    A          P
CynM         P  P  T          A G        P
Rt      --------  G L  VTD LPG  D P   Q  N              D
Mo      --------  G    VTD L    N P   Q  N              D
GP      ------DV     V V EPAV     P    S                D
Rb      ------     Q V VPE  AR KA  P                  S D
Cow     DM GELGP  -   LTT  PRGKDS  P  Q                 D
Dog*       Q EL P --------AG  T     P A  A              D      G
SeaL    EL   E  P --------AG    A   P    A              D

HU      LLSSQVTQELRALMDETMKELKAYKSELEEQLTPVAEETRARLSKELQAA  100
Ba            P      TT                   S
CynM          P      TT                   S
Rt          Q        TV  ED  T V     K    G             A   V  T
Mo          Q        T   ED  T V     K    G                G   V
GP            N      TL  IED   V D  A  KE G         D K    A
Rb                   TM  E     V          S M Q            V
Cow         NT   I   T   E     V      E   G M Q    Q       V
Dog     V   NT       T         V      A D G MTS    Q       VA
SeaL    V   N        TT  E     I      RA  G M S    Q       VA

HU      QARLGADMEDVRGRLVQYRGEVQAMLGQSTEELRVRLASHLRKLRKRLLR  150
Ba                  S       S                  A
CynM                S       S                  A
Rt              L N G     N    NT             S   ST    M      M
Mo              L N G     N    HT             A   ST    M      M
GP                E N S   S           S       A   T  P  M      Q
Rb          E       CN  A       A             A   FS
Cow       S         LC  A       S             A   M         P
Dog         R       N   T       L      S      A   F     M      V
SeaL               RS   T       S                 A F   M      V

HU      DADDLQKRLAVYQAGAREGAERGLSAIRERLGPLVEQGRVRAATVGSLAG  200
Ba                           V                               S
CynM                         V                               S
Rt                   K    Q  V                    Q T  NL AG A
Mo          E        K       V                    Q T  NL AG A
GP      I E     M    K    Q  V          S I       LQ ----- TS
Rb          E        M    G  V                L       L    ST
Cow                K         S       S        F       QS    LST
Dog         E    R   K    V     SV S       W  L   A E N K   A  T
SeaL        E            R   V  SV T       W  L   A T H K  DA  T
```

FIG. 7B

```
Hu     QPLQERAQAWGERLRARMEEMGSRTRDRLDEVKEQVAEVRAKLEEQAQQI 250
Ba                     L
CynM                   L
Rt     RD      LSD I G L   V NQA       E   R  ME   S M    T
Mo     RD      FDIGL       V NQA       E   R  HME  S M    T
GP             QM  G L KV    QA        E   R  ME    V V
Rb              GHL   V      A         E      E     V V   A M
Cow    R        RQK HG L V V AQ         KIRQ LE   H V    GN M
Dog    L   E    D  QQ  GQL  S  A GH E MR      IQ    V M   D
SeaL   L   D    VN L QQ  G L V  A SH       R  ME    Q M   N M
       R

Hu     RLQAEAFQARLKSWFEPLVEDMQRQWAGLVEKVQAAVGTSAAPVPSDNH 299  (SEQ ID NO:2)
Ba     S                                 A T                 (SEQ ID NO:3)
CynM   S                                 A T                 (SEQ ID NO:4)
Rt          I       I G            N M I    I  S A NSIASTTVPLENQ  (SEQ ID NO:5)
Mo          I         G        I   N M I       S A NPIIT VAQ-ENQ  (SEQ ID NO:6)
GP     -----G              MM R     N IQ    V    A TS-A  QEP     (SEQ ID NO:7)
Rb                                          L    MPSK PAAAPIENQ  (SEQ ID NO:8)
Cow              R                                L LRP PTSP  E  (SEQ ID NO:9)
Dog    QK                  L       D                A IPTSKPVEEP (SEQ ID NO:10)
SeaL   Q                G            V                PTTP VETK  (SEQ ID NO:11)
```

FIG. 11

DsRed-encoding nucleotide sequence

```
atggcctcct ccgagaacgt catcaccgag ttcatgcgct tcaaggtgcg catggagggc    60
accgtgaacg gccacgagtt cgagatcgag ggcgagggcg aggccgccc  ctacgagggc   120
cacaacaccg tgaagctgaa ggtgaccaag ggcggcccc  tgcccttcgc ctgggacatc   180
ctgtcccccc agttccagta cggctccaag gtgtacgtga agcaccccgc cgacatcccc   240
gactacaaga agctgtcctt ccccgagggc ttcaagtggg agcgcgtgat gaacttcgag   300
gacggcggcg tggcgaccgt gaccaggac  tcctccctgc aggacggctg cttcatctac   360
aaggtgaagt tcatcggcgt gaacttcccc tccgacggcc ccgtgatgca gaagaagacc   420
atgggctggg aggcctccac cgagcgcctg taccccgcg  acggcgtgct gaagggcgag   480
acccacaagg ccctgaagct gaaggacggc ggctactacc tggtggagtt caagtccatc   540
tacatggcca agaagcccgt gcagctgccc ggctactact acgtggacgc caagctggac   600
atcacctccc acaacgagga ctacaccatc gtggagcagt acgagcgcac cgagggccgc   660
caccacctgt tcctg                                                    675
```

(SEQ ID NO:24)

FIG. 17
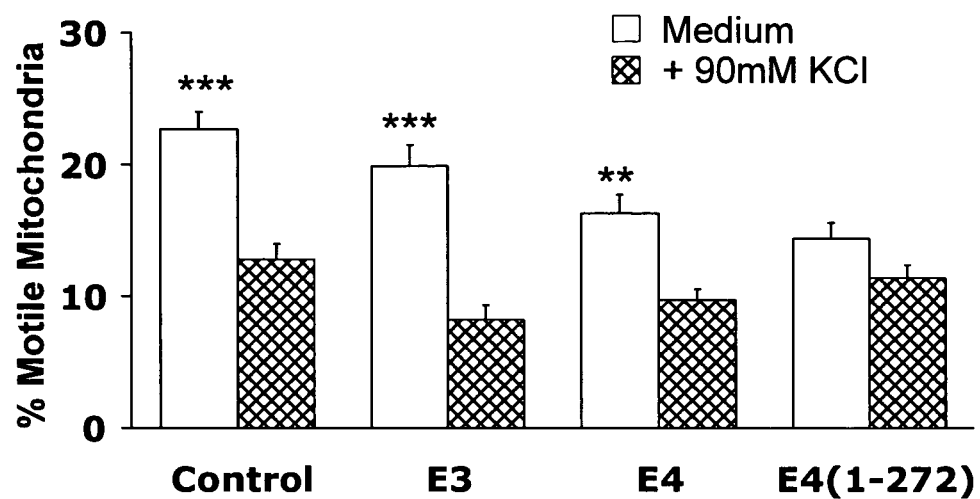
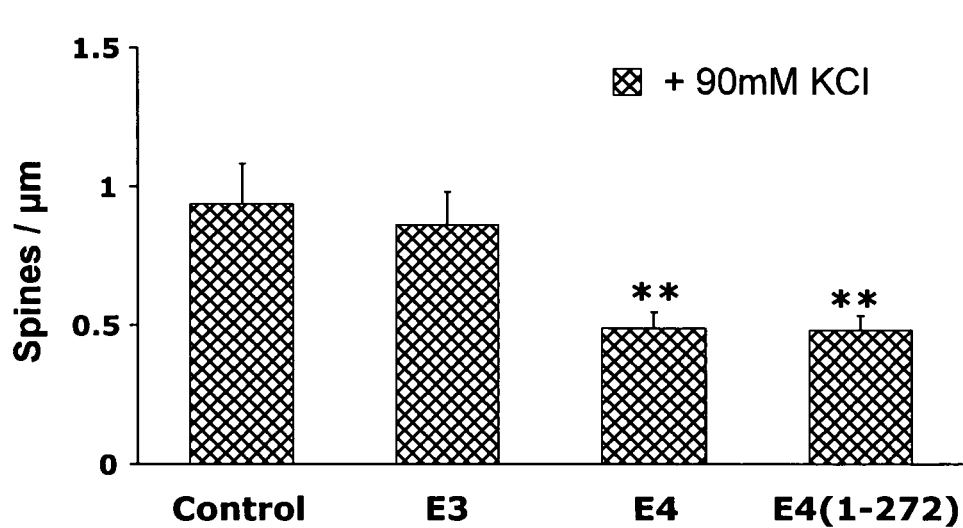

FIG. 19
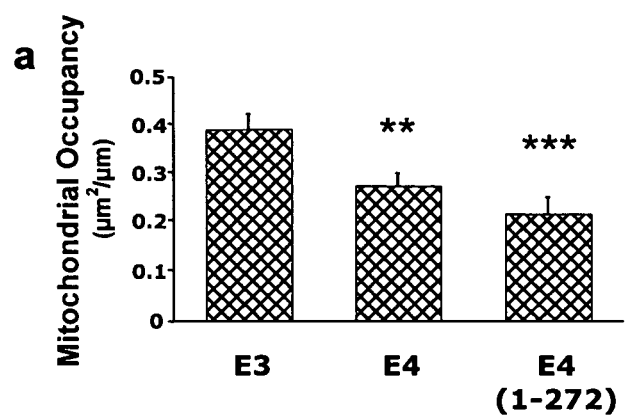
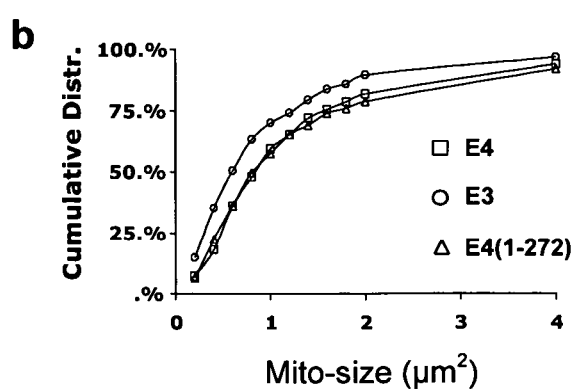

SEQUENCE LISTING

<160> NUMBER OF SEQ ID NOS: 25

<210> SEQ ID NO 1
<211> LENGTH: 299
<212> TYPE: PRT
<213> ORGANISM: H. sapiens

<400> SEQUENCE: 1

```
Lys Val Glu Gln Ala Val Glu Thr Glu Pro Glu Pro Glu Leu Arg Gln
 1               5                  10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295
```

<210> SEQ ID NO 2
<211> LENGTH: 299
<212> TYPE: PRT
<213> ORGANISM: H. sapiens

<400> SEQUENCE: 2

```
Lys Val Glu Gln Ala Val Glu Thr Glu Pro Glu Pro Glu Leu Arg Gln
 1               5                  10                  15
```

-continued

```
Gln Thr Glu Trp Gln Ser Gly Gln Arg Trp Glu Leu Ala Leu Gly Arg
             20                  25                  30

Phe Trp Asp Tyr Leu Arg Trp Val Gln Thr Leu Ser Glu Gln Val Gln
             35                  40                  45

Glu Glu Leu Leu Ser Ser Gln Val Thr Gln Glu Leu Arg Ala Leu Met
 50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Thr Arg Ala Arg Leu Ser Lys Glu
             85                  90                  95

Leu Gln Ala Ala Gln Ala Arg Leu Gly Ala Asp Met Glu Asp Val Arg
                100                 105                 110

Gly Arg Leu Val Gln Tyr Arg Gly Glu Val Gln Ala Met Leu Gly Gln
                115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
                195                 200                 205

Ala Trp Gly Glu Arg Leu Arg Ala Arg Met Glu Glu Met Gly Ser Arg
210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
                275                 280                 285

Thr Ser Ala Ala Pro Val Pro Ser Asp Asn His
    290                 295
```

<210> SEQ ID NO 3
<211> LENGTH: 299
<212> TYPE: PRT
<213> ORGANISM: baboon

<400> SEQUENCE: 3

```
Lys Val Glu Gln Pro Val Glu Pro Glu Thr Glu Pro Asp Val Arg Gln
  1               5                  10                  15

Gln Ala Glu Trp Gln Ser Gly Gln Pro Trp Glu Leu Ala Leu Gly Arg
             20                  25                  30

Phe Trp Asp Tyr Leu Arg Trp Val Gln Thr Leu Ser Glu Gln Val Gln
             35                  40                  45

Glu Glu Leu Leu Ser Pro Gln Val Thr Gln Glu Leu Thr Thr Leu Met
 50                  55                  60

Asp Glu Thr Met Lys Glu Leu Lys Ala Tyr Lys Ser Glu Leu Glu Glu
 65                  70                  75                  80

Gln Leu Ser Pro Val Ala Glu Glu Thr Arg Ala Arg Leu Ser Lys Glu
             85                  90                  95
```

```
Leu Gln Ala Ala Gln Ala Arg Leu Gly Ala Asp Met Glu Asp Val Arg
                100                 105                 110

Ser Arg Leu Val Gln Tyr Arg Ser Glu Val Gln Ala Met Leu Gly Gln
            115                 120                 125

Ser Thr Glu Glu Leu Arg Ala Arg Leu Ala Ser His Leu Arg Lys Leu
        130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Val Ser Ala
                165                 170                 175

Ile Arg Glu Arg Leu Gly Pro Leu Val Glu Gln Gly Val Arg Ala
            180                 185                 190

Ala Thr Val Gly Ser Leu Ala Ser Gln Pro Leu Gln Glu Arg Ala Gln
        195                 200                 205

Ala Leu Gly Glu Arg Leu Arg Ala Arg Met Glu Glu Met Gly Ser Arg
210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Ser Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Ala Ser Thr Ala Pro Val Pro Ser Asp Asn His
290                 295

<210> SEQ ID NO 4
<211> LENGTH: 299
<212> TYPE: PRT
<213> ORGANISM: cynomolgus monkey

<400> SEQUENCE: 4

Lys Val Glu Gln Pro Val Glu Pro Thr Glu Pro Glu Leu Arg Gln
1               5                   10                  15

Gln Ala Glu Gly Gln Ser Gly Gln Pro Trp Glu Leu Ala Leu Gly Arg
                20                  25                  30

Phe Trp Asp Tyr Leu Arg Trp Val Gln Thr Leu Ser Glu Gln Val Gln
            35                  40                  45

Glu Glu Leu Leu Ser Pro Gln Val Thr Gln Glu Leu Thr Thr Leu Met
50                  55                  60

Asp Glu Thr Met Lys Glu Leu Lys Ala Tyr Lys Ser Glu Leu Glu Glu
65                  70                  75                  80

Gln Leu Ser Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Arg
            100                 105                 110

Ser Arg Leu Val Gln Tyr Arg Ser Glu Val Gln Ala Met Leu Gly Gln
        115                 120                 125

Ser Thr Glu Glu Leu Arg Ala Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Val Ser Ala
                165                 170                 175
```

```
Ile Arg Glu Arg Leu Gly Pro Leu Val Glu Gln Gly Arg Val Arg Ala
            180                 185                 190

Ala Thr Val Gly Ser Leu Ala Ser Gln Pro Leu Gln Glu Arg Ala Gln
            195                 200                 205

Ala Leu Gly Glu Arg Leu Arg Ala Arg Met Glu Glu Met Gly Ser Arg
            210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Ser Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
                275                 280                 285

Ala Ser Thr Ala Pro Val Pro Ile Asp Asn His
                290                 295

<210> SEQ ID NO 5
<211> LENGTH: 293
<212> TYPE: PRT
<213> ORGANISM: rat

<400> SEQUENCE: 5

Glu Gly Glu Leu Glu Val Thr Asp Gln Leu Pro Gly Gln Ser Asp Gln
  1               5                  10                  15

Pro Trp Glu Gln Ala Leu Asn Arg Phe Trp Asp Tyr Leu Arg Trp Val
             20                  25                  30

Gln Thr Leu Ser Asp Gln Val Gln Glu Glu Leu Gln Ser Ser Gln Val
             35                  40                  45

Thr Gln Glu Leu Thr Val Leu Met Glu Asp Thr Met Thr Glu Val Lys
 50                  55                  60

Ala Tyr Lys Lys Glu Leu Glu Glu Gln Leu Gly Pro Val Ala Glu Glu
 65                  70                  75                  80

Thr Arg Ala Arg Leu Thr Lys Glu Val Gln Ala Ala Gln Ala Arg Leu
                 85                  90                  95

Gly Ala Asp Met Glu Asp Leu Arg Asn Arg Leu Gly Gln Tyr Arg Asn
            100                 105                 110

Glu Val Asn Thr Met Leu Gly Gln Ser Thr Glu Glu Leu Arg Ser Arg
            115                 120                 125

Leu Ser Thr His Leu Arg Lys Met Arg Lys Arg Leu Met Arg Asp Ala
130                 135                 140

Asp Asp Leu Gln Lys Arg Leu Ala Val Tyr Lys Ala Gly Ala Gln Glu
145                 150                 155                 160

Gly Ala Glu Arg Gly Val Ser Ala Ile Arg Glu Arg Leu Gly Pro Leu
                165                 170                 175

Val Glu Gln Gly Arg Gln Arg Thr Ala Asn Leu Arg Trp Arg Arg Pro
            180                 185                 190

Ala Pro Arg Asp Arg Ala Gln Ala Leu Ser Asp Arg Ile Arg Gly Arg
            195                 200                 205

Leu Glu Glu Val Gly Asn Gln Ala Arg Asp Leu Glu Glu Val Arg
            210                 215                 220

Glu Gln Met Glu Glu Val Arg Ser Lys Met Glu Glu Gln Thr Gln Gln
225                 230                 235                 240

Ile Arg Leu Gln Ala Glu Ile Phe Gln Ala Arg Ile Lys Gly Trp Phe
                245                 250                 255
```

-continued

```
Glu Pro Leu Val Glu Asp Met Gln Arg Gln Trp Ala Asn Leu Met Glu
            260                 265                 270
Lys Ile Gln Ala Ser Val Ala Thr Asn Ser Ile Ala Ser Thr Thr Val
        275                 280                 285
Pro Leu Glu Asn Gln
    290

<210> SEQ ID NO 6
<211> LENGTH: 293
<212> TYPE: PRT
<213> ORGANISM: mouse

<400> SEQUENCE: 6

Glu Gly Glu Pro Glu Val Thr Asp Gln Leu Glu Trp Gln Ser Asn Gln
  1               5                  10                  15
Pro Trp Glu Gln Ala Leu Asn Arg Phe Trp Asp Tyr Leu Arg Trp Val
             20                  25                  30
Gln Thr Leu Ser Asp Gln Val Gln Glu Leu Gln Ser Ser Gln Val
         35                  40                  45
Thr Gln Glu Leu Thr Ala Leu Met Glu Asp Thr Met Thr Glu Val Lys
 50                  55                  60
Ala Tyr Lys Lys Glu Leu Glu Glu Gln Leu Gly Pro Val Ala Glu Glu
 65                  70                  75                  80
Thr Arg Ala Arg Leu Gly Lys Glu Val Gln Ala Ala Gln Ala Arg Leu
                 85                  90                  95
Gly Ala Asp Met Glu Asp Leu Arg Asn Arg Leu Gly Gln Tyr Arg Asn
            100                 105                 110
Glu Val His Thr Met Leu Gly Gln Ser Thr Glu Glu Ile Arg Ala Arg
        115                 120                 125
Leu Ser Thr His Leu Arg Lys Met Arg Lys Arg Leu Met Arg Asp Ala
130                 135                 140
Asp Asp Leu Gln Lys Arg Leu Ala Val Tyr Lys Ala Gly Ala Arg Glu
145                 150                 155                 160
Gly Ala Glu Arg Gly Val Ser Ala Ile Arg Glu Arg Leu Gly Pro Leu
                165                 170                 175
Val Glu Gln Gly Arg Gln Arg Thr Ala Asn Leu Gly Ala Gly Ala Ala
            180                 185                 190
Gln Pro Leu Arg Asp Arg Ala Gln Ala Phe Gly Asp Arg Ile Arg Gly
        195                 200                 205
Arg Leu Glu Glu Val Gly Asn Gln Ala Arg Asp Arg Leu Glu Glu Val
210                 215                 220
Arg Glu His Met Glu Glu Val Arg Ser Lys Met Glu Glu Gln Thr Gln
225                 230                 235                 240
Gln Ile Arg Leu Gln Ala Glu Ile Phe Gln Ala Arg Leu Lys Gly Trp
                245                 250                 255
Phe Glu Pro Ile Val Glu Asp Met His Arg Gln Trp Ala Asn Leu Met
            260                 265                 270
Glu Lys Ile Gln Ala Ser Val Ala Thr Asn Pro Ile Ile Thr Pro Val
        275                 280                 285
Ala Gln Glu Asn Gln
    290

<210> SEQ ID NO 7
<211> LENGTH: 280
<212> TYPE: PRT
<213> ORGANISM: guinea pig
```

<400> SEQUENCE: 7

```
Asp Val Glu Pro Glu Val Glu Val Arg Glu Pro Ala Val Trp Gln Ser
  1               5                  10                  15

Gly Gln Pro Trp Glu Leu Ala Leu Ser Arg Phe Trp Asp Tyr Leu Arg
                 20                  25                  30

Trp Val Gln Thr Leu Ser Asp Gln Val Gln Glu Glu Leu Leu Ser Asn
             35                  40                  45

Gln Val Thr Gln Glu Leu Thr Leu Leu Ile Glu Asp Thr Met Lys Glu
         50                  55                  60

Val Lys Ala Tyr Lys Ala Glu Leu Glu Lys Glu Leu Gly Pro Val Ala
 65                  70                  75                  80

Glu Asp Thr Lys Ala Arg Leu Ala Lys Glu Leu Gln Ala Ala Gln Ala
                 85                  90                  95

Arg Leu Gly Ala Asp Met Glu Val Arg Asn Arg Leu Ser Gln Tyr
                100                 105                 110

Arg Ser Glu Val Gln Ala Met Leu Gly Gln Ser Ser Glu Glu Leu Arg
            115                 120                 125

Ala Arg Leu Thr Ser His Pro Arg Lys Met Lys Arg Leu Gln Arg
        130                 135                 140

Asp Ile Asp Glu Leu Gln Lys Arg Met Ala Val Tyr Lys Ala Gly Ala
145                 150                 155                 160

Gln Glu Gly Ala Glu Arg Gly Val Ser Ala Ile Arg Glu Arg Leu Gly
                165                 170                 175

Ser Leu Ile Glu Gln Gly Arg Leu Gln Ala Leu Ala Ser Gln Pro Leu
            180                 185                 190

Gln Glu Arg Ala Gln Ala Trp Gly Glu Gln Met Arg Gly Arg Leu Glu
        195                 200                 205

Lys Val Gly Ser Gln Ala Arg Asp Arg Leu Glu Glu Val Arg Glu Gln
210                 215                 220

Met Glu Glu Val Arg Val Lys Val Glu Glu Gln Ala Glu Ala Phe Gln
225                 230                 235                 240

Ala Arg Leu Lys Ser Trp Phe Glu Pro Met Met Glu Asp Met Arg Arg
                245                 250                 255

Gln Trp Ala Glu Leu Ile Gln Lys Val Gln Val Ala Val Gly Ala Ser
            260                 265                 270

Thr Ser Ala Pro Ser Gln Glu Pro
        275                 280
```

<210> SEQ ID NO 8
<211> LENGTH: 293
<212> TYPE: PRT
<213> ORGANISM: rabbit

<400> SEQUENCE: 8

```
Glu Thr Glu Gln Glu Val Glu Val Pro Glu Gln Ala Arg Trp Lys Ala
  1               5                  10                  15

Gly Gln Pro Trp Glu Leu Ala Leu Gly Arg Phe Trp Asp Tyr Leu Arg
                 20                  25                  30

Trp Val Gln Ser Leu Ser Asp Gln Val Gln Glu Glu Leu Leu Ser Ser
             35                  40                  45

Gln Val Thr Gln Glu Leu Thr Met Leu Met Glu Thr Met Lys Glu
         50                  55                  60

Val Lys Ala Tyr Lys Ser Glu Leu Glu Glu Gln Leu Ser Pro Met Ala
 65                  70                  75                  80

Gln Glu His Arg Ala Arg Leu Ser Lys Glu Leu Gln Val Ala Gly Ala
```

```
                    85                  90                  95
Leu Glu Ala Asp Met Glu Asp Val Cys Asn Arg Leu Ala Gln Tyr Arg
                100                 105                 110

Gly Glu Ala Gln Ala Met Leu Gly Gln Ser Thr Glu Glu Leu Ala Arg
            115                 120                 125

Ala Phe Ser Ser His Leu Arg Lys Leu Arg Lys Leu Leu Arg Asp
    130                 135                 140

Ala Glu Asp Leu Gln Lys Arg Met Ala Val Tyr Gly Ala Gly Ala Arg
145                 150                 155                 160

Glu Gly Ala Glu Arg Gly Val Ser Ala Val Arg Glu Arg Leu Gly Ser
                165                 170                 175

Arg Leu Glu Arg Gly Arg Leu Arg Val Ala Thr Val Gly Thr Leu Ala
            180                 185                 190

Gly Arg Pro Leu Arg Glu Arg Ala Gln Ala Trp Gly Glu Arg Leu Arg
        195                 200                 205

Gly His Leu Glu Glu Val Gly Ser Arg Ala Arg Asp Arg Leu Asn Glu
    210                 215                 220

Val Arg Glu Gln Val Glu Glu Val Arg Val Lys Val Glu Glu Gln Ala
225                 230                 235                 240

Pro Gln Met Arg Leu Gln Ala Glu Ala Phe Gln Ala Arg Leu Lys Ser
                245                 250                 255

Trp Phe Glu Pro Leu Val Glu Asp Met Gln Arg Gln Trp Ala Gly Leu
            260                 265                 270

Val Glu Lys Leu Gln Ala Ala Met Pro Ser Lys Ala Pro Ala Ala Ala
        275                 280                 285

Pro Ile Glu Asn Gln
    290

<210> SEQ ID NO 9
<211> LENGTH: 298
<212> TYPE: PRT
<213> ORGANISM: cow

<400> SEQUENCE: 9

Asp Met Glu Gly Glu Leu Gly Pro Glu Glu Pro Leu Thr Thr Gln Gln
1               5                   10                  15

Pro Arg Gly Lys Asp Ser Gln Pro Trp Glu Gln Ala Leu Gly Arg Phe
            20                  25                  30

Trp Asp Tyr Leu Arg Trp Val Gln Thr Leu Ser Asp Gln Val Gln Glu
        35                  40                  45

Glu Leu Leu Asn Thr Gln Val Ile Gln Glu Leu Thr Ala Leu Met Glu
    50                  55                  60

Glu Thr Met Lys Glu Val Lys Ala Tyr Lys Glu Glu Leu Glu Gly Gln
65                  70                  75                  80

Leu Gly Pro Met Ala Gln Glu Thr Gln Ala Arg Val Ser Lys Glu Leu
                85                  90                  95

Gln Ala Ala Gln Ala Arg Leu Gly Ser Asp Met Glu Asp Leu Arg Asn
            100                 105                 110

Arg Leu Ala Gln Tyr Arg Ser Glu Val Gln Ala Met Leu Gly Gln Ser
        115                 120                 125

Thr Glu Glu Leu Arg Ala Arg Met Ala Ser His Leu Arg Lys Leu Pro
    130                 135                 140

Lys Arg Leu Leu Arg Asp Ala Asp Asp Leu Lys Lys Arg Leu Ala Val
145                 150                 155                 160

Tyr Gln Ala Gly Ala Ser Glu Gly Ala Glu Arg Ser Leu Ser Ala Ile
```

```
                    165                 170                 175
Arg Glu Arg Phe Gly Pro Leu Val Glu Gln Gly Gln Ser Arg Ala Ala
                180                 185                 190

Thr Leu Ser Thr Leu Ala Gly Gln Pro Leu Leu Glu Arg Ala Glu Ala
            195                 200                 205

Trp Arg Gln Lys Leu His Gly Arg Leu Glu Glu Val Gly Val Arg Ala
210                 215                 220

Gln Asp Arg Leu Asp Lys Ile Arg Gln Gln Leu Glu Glu Val His Ala
225                 230                 235                 240

Lys Val Glu Glu Gln Gly Asn Gln Met Arg Leu Gln Ala Glu Ala Phe
                245                 250                 255

Gln Ala Arg Leu Arg Ser Trp Phe Glu Pro Leu Val Glu Asp Met Gln
            260                 265                 270

Arg Gln Trp Ala Gly Leu Val Glu Lys Val Gln Leu Ala Leu Arg Pro
        275                 280                 285

Ser Pro Thr Ser Pro Pro Ser Glu Asn His
            290                 295
```

<210> SEQ ID NO 10
<211> LENGTH: 291
<212> TYPE: PRT
<213> ORGANISM: dog

<400> SEQUENCE: 10

```
Lys Val Gln Gln Glu Leu Glu Pro Glu Ala Gly Trp Gln Thr Gly Gln
1               5                   10                  15

Pro Trp Glu Ala Ala Leu Ala Arg Phe Trp Asp Tyr Leu Arg Trp Val
                20                  25                  30

Gln Thr Leu Ser Asp Gln Val Gln Glu Gly Val Leu Asn Thr Gln Val
            35                  40                  45

Thr Gln Glu Leu Thr Ala Leu Met Asp Glu Thr Met Lys Glu Val Lys
        50                  55                  60

Ala Tyr Lys Ala Glu Leu Asp Glu Gln Leu Gly Pro Met Thr Ser Glu
65                  70                  75                  80

Thr Gln Ala Arg Val Ala Lys Glu Leu Gln Ala Ala Gln Ala Arg Leu
                85                  90                  95

Arg Ala Asp Met Glu Asp Val Arg Asn Arg Leu Thr Gln Tyr Arg Gly
            100                 105                 110

Glu Leu Gln Ala Met Leu Gly Gln Ser Ser Glu Glu Leu Arg Ala Arg
        115                 120                 125

Phe Ala Ser His Met Arg Lys Leu Arg Lys Arg Val Leu Arg Asp Ala
130                 135                 140

Glu Asp Leu Gln Arg Arg Leu Ala Val Tyr Lys Ala Gly Val Arg Glu
145                 150                 155                 160

Gly Ala Glu Arg Ser Val Ser Ser Ile Arg Glu Arg Leu Trp Pro Leu
                165                 170                 175

Leu Glu Gln Ala Arg Glu Arg Asn Ala Lys Val Gly Ala Leu Ala Thr
            180                 185                 190

Gln Pro Leu Leu Glu Arg Ala Asp Ala Trp Gly Gln Leu Arg Gly
        195                 200                 205

Gln Leu Glu Glu Met Ser Ser Arg Ala Arg Gly His Leu Glu Glu Met
        210                 215                 220

Arg Glu Gln Ile Gln Glu Val Arg Val Lys Met Glu Glu Gln Ala Asp
225                 230                 235                 240

Gln Ile Arg Gln Lys Ala Glu Ala Phe Gln Ala Arg Leu Lys Ser Trp
```

```
                        245                 250                 255
Phe Glu Pro Leu Leu Glu Asp Met Gln Arg Gln Trp Asp Gly Leu Val
            260                 265                 270

Glu Lys Val Gln Ala Ala Val Ala Thr Ile Pro Thr Ser Lys Pro Val
            275                 280                 285

Glu Glu Pro
    290

<210> SEQ ID NO 11
<211> LENGTH: 291
<212> TYPE: PRT
<213> ORGANISM: sea lion

<400> SEQUENCE: 11

Glu Leu Glu Gln Glu Val Glu Pro Glu Ala Gly Trp Gln Ala Gly Gln
  1               5                  10                  15

Pro Trp Glu Leu Ala Leu Ala Arg Phe Trp Asp Tyr Leu Arg Trp Val
             20                  25                  30

Gln Thr Leu Ser Asp Gln Val Gln Glu Glu Val Leu Ser Asn Gln Val
         35                  40                  45

Thr Gln Glu Leu Thr Thr Leu Met Glu Glu Thr Met Lys Glu Ile Lys
 50                  55                  60

Ala Tyr Arg Ala Glu Leu Glu Glu Gln Leu Gly Pro Met Ala Ser Glu
 65                  70                  75                  80

Thr Gln Ala Arg Val Ala Lys Glu Leu Gln Ala Ala Gln Ala Arg Leu
                 85                  90                  95

Arg Ser Asp Met Glu Asp Val Arg Thr Arg Leu Ser Gln Tyr Arg Gly
            100                 105                 110

Glu Val Gln Ala Met Leu Gly Gln Ser Thr Glu Glu Leu Arg Ala Arg
        115                 120                 125

Phe Ala Ser His Met Arg Lys Leu Arg Lys Arg Val Leu Arg Asp Ala
    130                 135                 140

Glu Asp Leu Gln Lys Arg Leu Ala Val Tyr Arg Ala Gly Val Arg Glu
145                 150                 155                 160

Gly Ala Glu Arg Ser Val Ser Thr Ile Arg Glu Arg Leu Trp Pro Leu
                165                 170                 175

Leu Glu Gln Ala Arg Thr Arg His Ala Lys Val Asp Ala Leu Ala Thr
            180                 185                 190

Gln Pro Leu Arg Glu Arg Val Asn Ala Leu Gly Gln Gln Leu Arg Gly
        195                 200                 205

Arg Leu Glu Glu Val Gly Ser Arg Ala Arg Ser His Leu Asp Glu Val
    210                 215                 220

Arg Glu Gln Met Glu Glu Val Gln Ala Lys Met Glu Glu Gln Ala Asn
225                 230                 235                 240

Gln Met Arg Gln Gln Ala Glu Ala Phe Gln Ala Arg Leu Lys Gly Trp
                245                 250                 255

Phe Glu Pro Leu Val Glu Asp Met Gln Arg Gln Trp Ala Val Leu Val
            260                 265                 270

Glu Lys Val Gln Ala Ala Val Gly Thr Ser Pro Thr Thr Pro Pro Val
        275                 280                 285

Glu Thr Lys
    290

<210> SEQ ID NO 12
<211> LENGTH: 14
<212> TYPE: PRT
```

```
<213> ORGANISM: dog

<400> SEQUENCE: 12

Asp Val Gln Pro Glu Pro Glu Leu Glu Arg Glu Leu Glu Pro
1               5                   10

<210> SEQ ID NO 13
<211> LENGTH: 16
<212> TYPE: PRT
<213> ORGANISM: sea lion

<400> SEQUENCE: 13

Asp Val Glu Pro Glu Ser Pro Leu Glu Glu Asn Leu Glu Pro Glu Leu
1               5                   10                  15

<210> SEQ ID NO 14
<211> LENGTH: 4
<212> TYPE: PRT
<213> ORGANISM: sea lion

<400> SEQUENCE: 14

Glu Pro Lys Arg
1

<210> SEQ ID NO 15
<211> LENGTH: 10
<212> TYPE: PRT
<213> ORGANISM: Artificial Sequence
<220> FEATURE:
<223> OTHER INFORMATION: epitope tag

<400> SEQUENCE: 15

Cys Tyr Pro Tyr Asp Val Pro Asp Tyr Ala
1               5                   10

<210> SEQ ID NO 16
<211> LENGTH: 8
<212> TYPE: PRT
<213> ORGANISM: Artificial Sequence
<220> FEATURE:
<223> OTHER INFORMATION: epitope tag

<400> SEQUENCE: 16

Asp Tyr Lys Asp Asp Asp Asp Lys
1               5

<210> SEQ ID NO 17
<211> LENGTH: 11
<212> TYPE: PRT
<213> ORGANISM: Artificial Sequence
<220> FEATURE:
<223> OTHER INFORMATION: epitope tag

<400> SEQUENCE: 17

Cys Glu Gln Lys Leu Ile Ser Glu Glu Asp Leu
1               5                   10

<210> SEQ ID NO 18
<211> LENGTH: 27
<212> TYPE: PRT
<213> ORGANISM: Artificial Sequence
<220> FEATURE:
<223> OTHER INFORMATION: Fragment of human protein

<400> SEQUENCE: 18

Gln Arg Gln Trp Ala Gly Leu Val Glu Lys Val Gln Ala Ala Val Gly
1               5                   10                  15
```

Thr Ser Ala Ala Pro Val Pro Ser Asp Asn His
            20                  25

<210> SEQ ID NO 19
<211> LENGTH: 25
<212> TYPE: PRT
<213> ORGANISM: Artificial Sequence
<220> FEATURE:
<223> OTHER INFORMATION: Fragment of human protein

<400> SEQUENCE: 19

Gln Arg Gln Trp Ala Gly Leu Val Glu Lys Val Gln Ala Ala Val Gly
1               5                   10                  15

Thr Ser Ala Ala Pro Val Pro Ser Asp
            20                  25

<210> SEQ ID NO 20
<211> LENGTH: 22
<212> TYPE: PRT
<213> ORGANISM: Artificial Sequence
<220> FEATURE:
<223> OTHER INFORMATION: Fragment of human protein

<400> SEQUENCE: 20

Gln Arg Gln Trp Ala Gly Leu Val Glu Lys Val Gln Ala Ala Val Gly
1               5                   10                  15

Thr Ser Ala Ala Pro Val
            20

<210> SEQ ID NO 21
<211> LENGTH: 23
<212> TYPE: PRT
<213> ORGANISM: Artificial Sequence
<220> FEATURE:
<223> OTHER INFORMATION: Fragment of human protein

<400> SEQUENCE: 21

Ala Gly Leu Val Glu Lys Val Gln Ala Ala Val Gly Thr Ser Ala Ala
1               5                   10                  15

Pro Val Pro Ser Asp Asn His
            20

<210> SEQ ID NO 22
<211> LENGTH: 23
<212> TYPE: PRT
<213> ORGANISM: Artificial Sequence
<220> FEATURE:
<223> OTHER INFORMATION: Fragment of human protein

<400> SEQUENCE: 22

Trp Ala Gly Leu Val Glu Lys Val Gln Ala Ala Val Gly Thr Ser Ala
1               5                   10                  15

Ala Pro Val Pro Ser Asp Asn
            20

<210> SEQ ID NO 23
<211> LENGTH: 21
<212> TYPE: PRT
<213> ORGANISM: Artificial Sequence
<220> FEATURE:
<223> OTHER INFORMATION: Fragment of human protein

<400> SEQUENCE: 23

Trp Ala Gly Leu Val Glu Lys Val Gln Ala Ala Val Gly Thr Ser Ala
1               5                   10                  15

```
Ala Pro Val Pro Ser
            20

<210> SEQ ID NO 24
<211> LENGTH: 675
<212> TYPE: DNA
<213> ORGANISM: Artificial Sequence
<220> FEATURE:
<223> OTHER INFORMATION: Encodes non-aggregating mutant of a Discosoma
      protein

<400> SEQUENCE: 24
atggcctcct ccgagaacgt catcaccgag ttcatgcgct tcaaggtgcg catggagggc      60
accgtgaacg gccacgagtt cgagatcgag ggcgagggcg agggccgccc ctacgagggc     120
cacaacaccg tgaagctgaa ggtgaccaag ggcggcccc  tgcccttcgc ctgggacatc     180 ctgtccccc  agttccagta cggctccaag gtgtacgtga agcacccgc  cgacatcccc     240 gactacaaga agctgtcctt ccccgagggc ttcaagtggg agcgcgtgat gaacttcgag     300
gacggcggcg tggcgaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccgcg  acggcgtgct gaagggcgag     480
acccacaagg ccctgaagct gaaggacggc ggccactacc tggtggagtt caagtccatc     540
tacatggcca agaagcccgt gcagctgccc ggctactact acgtggacgc caagctggac     600
atcacctccc acaacgagga ctacaccatc gtggagcagt acgagcgcac cgagggccgc     660
caccacctgt cctg                                                       675

<210> SEQ ID NO 25
<211> LENGTH: 35
<212> TYPE: PRT
<213> ORGANISM: Artificial Sequence
<220> FEATURE:
<223> OTHER INFORMATION: Fragment of human protein

<400> SEQUENCE: 25

Met Gly Val Phe Cys Leu Gly Pro Trp Gly Leu Gly Arg Lys Leu Arg
1               5                   10                  15

Thr Pro Gly Lys Gly Pro Leu Gln Leu Leu Ser Arg Leu Cys Gly Asp
            20                  25                  30

His Leu Gln
        35
```

METHODS OF IDENTIFYING AGENTS THAT MODULATE MITOCHONDRIAL FUNCTION

CROSS-REFERENCE

This application claims the benefit of U.S. Provisional Patent Application No. 60/748,661, filed Dec. 7, 2005, which application is incorporated herein by reference in its entirety.

BACKGROUND OF THE INVENTION

Human apolipoprotein (apo) E, a 34-kDa protein with 299 amino acids, has three major isoforms, apoE2, apoE3, and apoE4 (1-4). apoE4 is a major risk factor for Alzheimer's disease (AD) (5-7). The apoE4 allele, which is found in 40-65% of cases of sporadic and familial AD, increases the occurrence and lowers the age of onset of the disease (7, 8).

Biochemical, cell biological, transgenic animal, and human studies have suggested several potential mechanisms to explain apoE4's contribution to the pathogenesis of AD. These include modulation of the deposition and clearance of amyloid beta (Aβ) peptides and the formation of plaques (9-15), modulation of Aβ-caused synaptic and cholinergic deficits (16), acceleration of age- and excitotoxicity-related neurodegeneration (17), impairment of the antioxidative defense system and mitochondrial function (18-21), dysregulation of neuronal signaling pathways (22), altered phosphorylation of tau and neurofibrillary tangle formation (23-28), depletion of cytosolic androgen receptor levels in the brain (29, 30), potentiation of Aβ-induced lysosomal leakage and apoptosis in neuronal cells (31), and promotion of endosomal abnormalities linked to Aβ overproduction (32-34). The mechanisms of these apoE4-mediated detrimental effects are largely unknown.

It has been shown that apoE can be cleaved by a neuron-specific chymotrypsin-like serine protease that generates bioactive carboxyl-terminal-truncated forms of apoE (25, 27, 28). The fragments are found at higher levels in the brains of AD patients than in age- and sex-matched controls (27), and apoE4 is more susceptible to cleavage than apoE3. When expressed in cultured neuronal cells or added exogenously to the cultures, apoE4 fragments are neurotoxic, leading to cell death (25). When expressed in transgenic mice, they cause AD-like neurodegeneration and behavioral deficits (27).

Alzheimer's disease is an insidious and progressive neurological disorder for which there is currently no cure. In view of the lack of adequate treatment for Alzheimer's disease, there exists a need for novel treatment methods for this neurological disorder. The instant invention provides methods of identifying agents for use in treating disorders relating to apoE4.

Literature

Huang et al. (2001) *Proc. Natl. Acad. Sci. USA* 98:8838-8843; U.S. Pat. No. 6,046,381.

SUMMARY OF THE INVENTION

The present invention provides isolated cells comprising a nucleic acid encoding a toxic form of apoE. The present invention further provides screening methods for identifying compounds that reduce apoE-induced impairment of mitochondrial integrity and/or function. The present invention further provides kits for use in carrying out a subject screening method. The present invention provides agents that reduce apoE-induced impairment of mitochondrial integrity and/or function; and use of such agents in the treatment of apoE-related disorders.

BRIEF DESCRIPTION OF THE DRAWINGS

FIG. 6 depicts an amino acid sequence of human apoE4 (SEQ ID NO:1).

FIGS. 7A and 7B depict amino acid sequences of various apoE polypeptides.

FIG. 11 provides a nucleotide sequence encoding a DsRed2 polypeptide.

FIGS. 17A and 17B depict the effect of apoE4 and its fragment on activity-dependent mitochondrial dynamics and synaptogenesis.

FIGS. 19A and 19B depict the effect of apoE4 and its fragment on occupancy of mitochondria in dendrites of primary cortical neurons.

DEFINITIONS

Figure 1:
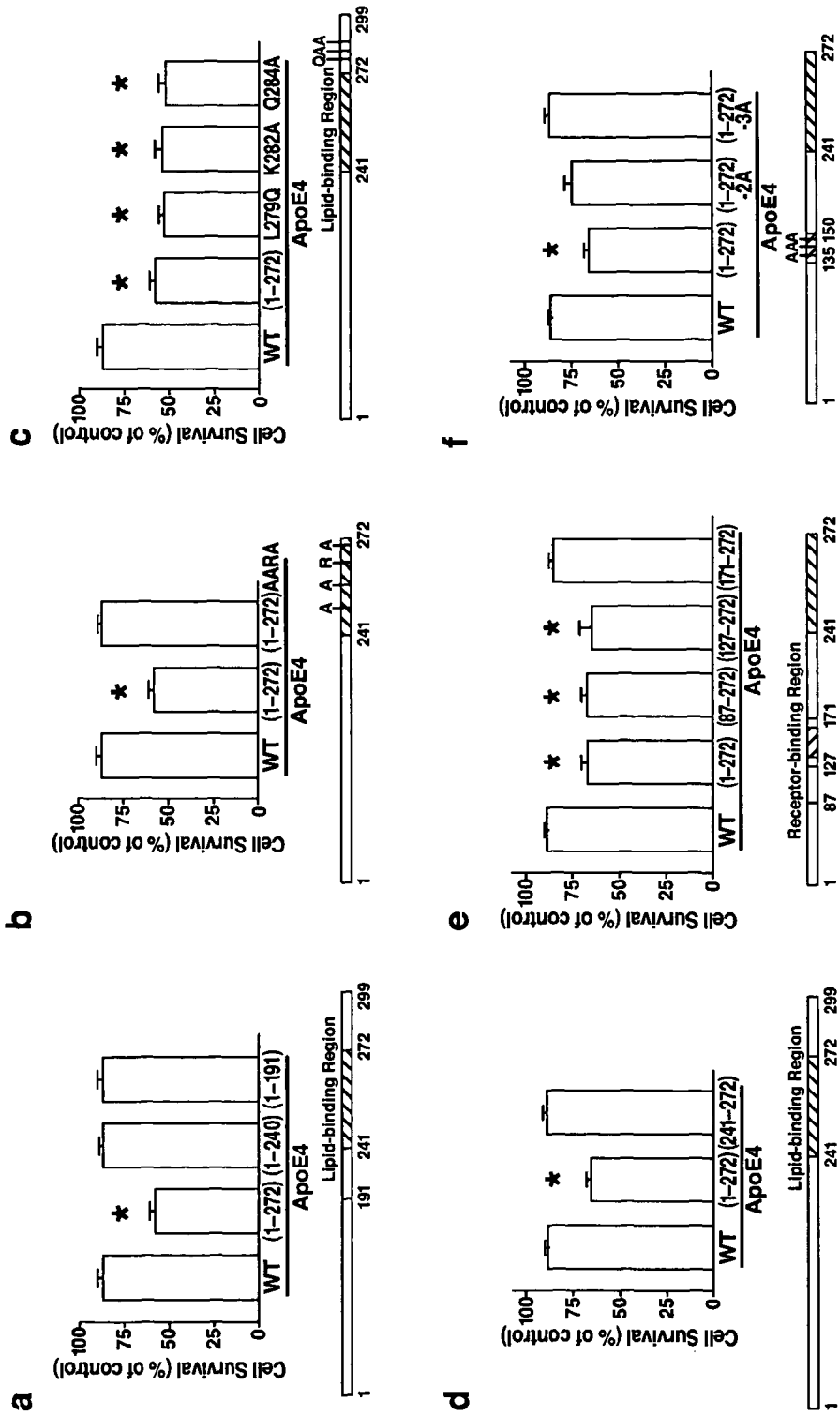
FIGS. 1A-1F depict the effect of apoE4 on survival of neuronal cells.

As used herein, an "apoE4-associated disorder" is any disorder that is caused by the presence of apoE4 in a cell, in the serum, in the interstitial fluid, in the cerebrospinal fluid, or in any other bodily fluid of an individual; any physiological process or metabolic event that is influenced by neurotoxic apoE4 polypeptides; any disorder that is characterized by the presence of apoE4; a symptom of a disorder that is caused by the presence of apoE4 in a cell or in a bodily fluid; a phenomenon associated with a disorder caused by the presence in a cell or in a bodily fluid of apoE4; and the sequelae of any disorder that is caused by the presence of apoE4. ApoE4-associated disorders include apoE4-associated neurological disorders and disorders related to high serum lipid levels. ApoE4-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE4-associated neurological disorders include, but are not limited to, neurofibrillary tangles; amyloid deposits; memory loss; and a reduction in cognitive function. ApoE4-related disorders associated with high serum lipid levels include, but are not limited to, atherosclerosis, and coronary artery disease. Phenomena associated with such apoE4-associated disorders include high serum cholesterol levels.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," and "patient," used interchangeably herein, refer to a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a toxic apoE polypeptide" includes a plurality of such polypeptides and reference to "the indicator agent" includes reference to one or more indicator agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides isolated cells comprising a nucleic acid encoding a toxic form of apoE. The present invention further provides screening methods for identifying compounds that reduce apoE-induced impairment of mitochondrial integrity and/or function. The present invention further provides kits for use in carrying out a subject screening method. The present invention provides agents that reduce apoE-induced impairment of mitochondrial integrity and/or function; and use of such agents in the treatment of apoE-related disorders.

Isolated Cells

The present invention provides isolated cells comprising a nucleic acid encoding a toxic (e.g., neurotoxic) form of apoE. The cells typically comprise a nucleic acid comprising a nucleotide sequence encoding a toxic apoE polypeptide; and a regulatory element(s) operably linked to the nucleotide sequence encoding the toxic apoE polypeptide. The cells produce toxic apoE polypeptides, and are useful in screening methods for identifying agents that reduced apoE-induced impairment of mitochondrial integrity and/or function.

Toxic apoE polypeptide-induced impairment of mitochondrial integrity and/or function includes one or more of the following: 1) reduced number of mitochondria in dendrites of primary neurons; 2) reduced size of mitochondria in dendrites of primary neurons; 3) reduced membrane potential of mitochondria; 4) reduced mitochondrial motility; 5) reduced anterograde velocity of mitochondria; and 6) reduced mitochondrial size.

Nucleotide and amino acid sequences of apoE polypeptides are known in the art. Human apoE4 has the amino acid sequence set forth in FIG. 6 and SEQ ID NO:1. See, e.g., Rall et al. (1982) *J. Biol. Chem.* 257:4171-4178; and Weisgraber et al. ((1994) *Adv. Protein Chem.* 45:240-302. Sequences of apoE polypeptides from other species are depicted in FIGS. 7A and 7B. These sequences are also provided in Weisgraber et al. ((1994) supra). In some embodiments, the apoE polypeptide is a full-length apoE4 polypeptide. In some embodiments, the apoE polypeptide is a toxic fragment of an apoE4 polypeptide.

FIGS. 7A and 7B depict a comparison of amino acid sequences of apolipoprotein E from 10 species. Sequences are aligned against human apoE4. Hu, Human (Rall et al. (1982) *J. Biol. Chem.* 257:4171-4178; SEQ ID NO:1); Ba, baboon (Hixson et al. (1988) *Genomics* 2:315-323; SEQ ID NO:2); CynM, cynomolgus monkey (Marotti et al. (1989) *Nucleic Acids Res.* 17:1778; SEQ ID NO:3); Rt, rat (McLean et al. (1983) *J. Biol. Chem.* 258:8993-9000; SEQ ID NO:4); Mo, mouse (Rajavashisth et al. (1985) *Proc. Natl. Acad. Sci. USA* 82:8085-8089; SEQ ID NO:5); GP, guinea pig (Matsushima et al. (1990) *Nucl. Acids Res.* 18:202; SEQ ID NO:6); Rb, rabbit (Lee et al. (1991) *J. Lipid Res.* 32:165-171; SEQ ID NO:7); cow (Chan and Li (1991) *Curr. Opin. Lipidol.* 2:96-103; SEQ ID NO:8); dog (Luo et al. (1989) *J. Lipid Res.* 30:1735-1746; and Weisgraber et al. (1980) *Biochem. Biophys. Res. Commun.* 95:374-380; SEQ ID NO:9); SeaL, sea lion (Davis et al. (1991) *J. Lipid Res.* 32:1013-1023; SEQ ID NO:10). Blanks indicate identity to human sequence; dashes (−) indicate deletions inserted to maximize homology with the human sequence. One-letter amino acid designations are used. A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; S, serine; V, valine; W, tryptophan; Y, tyrosine. *, Dog sequence contains amino-terminal extension: DVQPEPELERELEP (SEQ ID NO:11); †, SeaL sequence contains amino-terminal extension: DVEPESPLEENLEPEL+EPKR (SEQ ID NO:12 and SEQ ID NO:13, respectively).

The sequence of the mouse apoE gene is found under Genbank accession number D00466. Various primate apoE gene sequences are found under GenBank accession numbers AF200508, AF200507, AF200506, and AH009953 (*Hylobates lar*, or gibbon); AH009952, AF200503, AF200504, and AF200505 (*Pongo pygmaeus*, or orangutan); AH009951, AF200500, AG200501, and AF200502 (*Gorilla gorilla*); AH009950, AF200497, AF200498, AF200499 (*Pan troglodytes*, or chimpanzee).

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest. Numerous suitable expression vectors are known to those of skill in the art, and many are commercially available. The following vectors are provided by way of example; for eukaryotic host cells: pXT1, pcDNA3.1, pSG5 (Stratagene), pSVK3, pBPV, pMSG, and pSVLSV40 (Pharmacia). However, any other plasmid or other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see, e.g., Bitter et al. (1987) Methods in Enzymology, 153:516-544). In some embodiments, regulatory elements include regulatory elements that result in neuronal cell-specific expression of the operably linked apoE polypeptide-encoding nucleic acid. Neuronal cell-specific regulatory elements (including promoters, enhancers, and the like) are known to those skilled in the art. Examples of neuronal cell-specific regulatory elements include those from a neuron-specific enolase (NSE) gene (Hannas-Djebarra et al. (1997) *Brain Res. Mol. Brain Res.* 46:91-99), and see, e.g., EMBL HSENO2, X51956; a PDGF gene; a Th1 gene (e.g., mouse Thy1.2 (Caroni et al. (1997) *J. Neurosci. Methods* 71:3-9); a neurofilament gene (e.g., NF-L, NF-M, and NF-L); a glial filament acidic protein (GFAP) gene; a myelin basic protein gene; a microtubule associated protein genes; a synaptophysin gene; a tyrosine hydroxylase gene; and the like. Thus, e.g., a suitable neuronal cell-specific regulator region includes, e.g., an NSE promoter; a PDGF promoter; an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a GFAP promoter; and a CMV enhancer/platelet-derived growth factor-β promoter (see, e.g., Liu et al. (2004) *Gene Therapy* 11:52-60).

In some embodiments, the toxic apoE polypeptide-encoding nucleotide sequence is operably linked to an inducible promoter. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., PBAD (see, e.g., Guzman et al. (1995) J. Bacteriol. 177:4121-4130); a xylose-inducible promoter, e.g., Pxyl (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., CI857-repressed lambda-based expression vectors; see, e.g., Hoffmann et al. (1999) FEMS Microbiol Lett. 177 (2): 327-34); and the like.

In addition, the expression vectors will in many embodiments contain one or more selectable marker genes to provide a phenotypic trait for selection of transformed host cells such as dihydrofolate reductase or neomycin resistance for eukaryotic cell culture.

The apoE-encoding nucleotide sequences are typically included in an expression vector that provides for expression of the apoE polypeptide-encoding nucleotide sequence and production of the apoE polypeptide in a eukaryotic cell. A wide variety of which are known in the art and need not be elaborated upon herein. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject expression vectors, or both.

To generate a genetically modified host cell, a construct comprising a nucleotide sequence encoding a toxic apoE polypeptide is introduced stably or transiently into a host cell, using established techniques, including, but not limited to, electroporation, calcium phosphate precipitation, DEAE-dextran mediated transfection, liposome-mediated transfection, heat shock in the presence of lithium acetate, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

Toxic apoE Polypeptides

As used herein, the term "toxic apoE polypeptide" includes full length apoE polypeptides, as well as fragments of an apoE polypeptide, that are neurotoxic and/or that induce impairment of mitochondrial integrity and/or that induce impairment of mitochondrial function. In some embodiments, a toxic apoE polypeptide is a toxic apoE4 polypeptide, or a toxic fragment of an apoE4 polypeptide.

Toxic apoE polypeptides typically include at least: 1) the lipid binding region of an apoE polypeptide, e.g., amino acids 241 to about 272 of SEQ ID NO:1, or a variant thereof; and 2) the receptor-binding region of an apoE polypeptide, e.g., amino acids 135 to about 150 of SEQ ID NO:1, or a variant thereof; and lack a functional neuroprotective carboxyl-terminal portion, e.g., amino acids 273-299 of SEQ ID NO:1, or a variant thereof. The lipid-binding portion comprises at least amino acids corresponding to I250, F257, W264, and V269 of SEQ ID NO:1. I250, F257, W264, and V269 are highly conserved in the lipid-binding regions of various apoE polypeptides. The receptor-binding portion comprises at least amino acids corresponding to R142, K146, and R147 of SEQ ID NO:1. R142, K146, and R147 are highly conserved in the receptor-binding regions of various apoE polypeptides. As noted above, in some embodiments, a suitable toxic apoE polypeptides typically lack amino acid 273-299 of an apoE polypeptide, e.g., lack amino acids 273-299 of the amino acid sequence set forth in SEQ ID NO:1.

For example, in some embodiments, a suitable toxic apoE polypeptide comprises an amino acid sequence having at least about 75%, at least about 80%, at least about 85%, at least about 90%, at least about 95%, at least about 98%, or at least about 99% amino acid sequence identity to amino acids 1-272 of SEQ ID NO:1, where the toxic apoE polypeptide comprises a lipid-binding region comprising at least amino acids corresponding to I250, F257, W264, and V269 of SEQ ID NO:1; where the toxic apoE polypeptide comprises a receptor-binding region comprising at least amino acids corresponding to R142, K146, and R147 of SEQ ID NO:1; and where the toxic apoE polypeptide lacks a carboxyl-terminal portion corresponding to amino acids 273-299 of SEQ ID NO:1.

Suitable toxic apoE polypeptides include, but are not limited to, a polypeptide comprising: amino acids 1-272; amino acids 10-272; amino acids 15-272; amino acids 25-272; amino acids 50-272; amino acids 75-272; amino acids 100-272; amino acids 125-272; or amino acids 135-272 of an apoE polypeptide, e.g., of SEQ ID NO:1, or a variant thereof. For example, suitable toxic apoE polypeptides include, but are not limited to, a polypeptide comprising: amino acids 1-272; amino acids 10-272; amino acids 15-272; amino acids 25-272; amino acids 50-272; amino acids 75-272; amino acids 100-272; amino acids 125-272; or amino acids 135-272 of an apoE polypeptide comprising an amino acid sequence having at least about 75%, at least about 80%, at least about 85%, at least about 90%, at least about 95%, at least about 98%, or at least about 99% amino acid sequence identity to a corresponding portion of SEQ ID NO:1 (e.g., amino acids 1-272; amino acids 10-272; amino acids 15-272; amino acids 25-272; amino acids 50-272; amino acids 75-272; amino acids 100-272; amino acids 125-272; or amino acids 135-272 of SEQ ID NO:1), where the toxic apoE polypeptide comprises a lipid-binding region comprising at least amino acids corresponding to I250, F257, W264, and V269 of SEQ ID NO:1; where the toxic apoE polypeptide comprises a receptor-binding region comprising at least amino acids corresponding to R142, K146, and R147 of SEQ ID NO:1; and where the toxic apoE polypeptide lacks a carboxyl-terminal portion corresponding to amino acids 273-299 of SEQ ID NO:1.

In other embodiments, a suitable toxic apoE polypeptide comprises an amino acid sequence having at least about 75%, at least about 80%, at least about 85%, at least about 90%, at least about 95%, at least about 98%, or at least about 99% amino acid sequence identity to amino acids 1-299 of SEQ ID NO:1, where the toxic apoE polypeptide comprises a lipid-binding region comprising at least amino acids corresponding to I250, F257, W264, and V269 of SEQ ID NO:1; where the toxic apoE polypeptide comprises a receptor-binding region comprising at least amino acids corresponding to R142, K146, and R147 of SEQ ID NO:1; and where the toxic apoE polypeptide comprises a carboxyl-terminal portion corresponding to amino acids 273-299 of SEQ ID NO:1, where the carboxyl-terminal portion lacks neuroprotective activity, e.g., where at least amino acid residues corresponding to L279, K282, and Q284 are mutated such that the carboxyl-terminal portion is not neuroprotective.

For example, in some embodiments, a suitable toxic apoE polypeptide comprises an amino acid sequence having at least about 75%, at least about 80%, at least about 85%, at least about 90%, at least about 95%, at least about 98%, or at least about 99% amino acid sequence identity to amino acids 1-299 of SEQ ID NO:1, where the toxic apoE polypeptide comprises a lipid-binding region comprising at least amino acids corresponding to I250, F257, W264, and V269 of SEQ ID NO:1; where the toxic apoE polypeptide comprises a receptor-binding region comprising at least amino acids corresponding to R142, K146, and R147 of SEQ ID NO:1; and where the toxic apoE polypeptide comprises a carboxyl-terminal portion corresponding to amino acids 273-299 of SEQ ID NO:1, where the carboxyl-terminal portion comprises at least L279Q, K272A, and Q284A mutations.

Toxic apoE polypeptides also include fusion proteins that include a toxic apoE polypeptide and a heterologous protein (a "fusion partner") fused in-frame to the amino terminus or carboxyl terminus of the toxic apoE polypeptide protein. Suitable fusion partners include peptides and polypeptides that provide ease of purification, e.g., $(His)_n$, e.g., 6His, and the like; provide an epitope tag, e.g., glutathione-S-transferase (GST), hemagglutinin (HA; e.g., CYPYDVPDYA; SEQ ID NO:15), FLAG (e.g., DYKDDDDK; SEQ ID NO:16), c-myc (e.g., CEQKLISEEDL; SEQ ID NO:17), and the like; peptides and polypeptides provide a detectable signal, e.g., an enzyme that generates a detectable product (e.g., β-galactosidase, luciferase, horse radish peroxidase, alkaline phosphatase, etc.), or a protein that is itself detectable, e.g., a fluorescent protein (e.g., a green fluorescent protein), a fluorescent protein from an Anthozoa species (see, e.g., Matz et al. (1999) *Nat. Biotechnol.* 17:969-973); and the like.

In some embodiments, the host cell is genetically modified with: 1) a nucleic acid comprising a nucleotide sequence encoding a toxic apoE polypeptide, as described above; and 2) a nucleic acid comprising a nucleotide sequence encoding a mitochondrial indicator polypeptide, e.g., a polypeptide that generates a detectable signal, where the polypeptide comprises an amino acid sequence that provides for mitochondrial localization of the mitochondrial indicator polypeptide. Suitable polypeptides that generate a detectable signal include, but are not limited to, fluorescent proteins, e.g., a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); a fluorescent protein as described in U.S. Pat. No. 6,969,597; any of a variety of fluorescent and colored proteins from Anthozoan species, as described in, e.g., Matz et al. (1999) *Nature Biotechnol.* 17:969-973; and the like. Suitable fluorescent proteins include, e.g., DsRed. See, e.g., Geoffrey S. Baird et al. "Biochemistry, mutagenesis, and oligomerization of DsRed, a red fluorescent protein from coral" *PNAS*, Oct. 24, 2000, vol. 97, No. 22 pp. 11984-11989. DsRed polypeptides and variants are also described in, e.g., U.S. Patent Publication No. 2005/0244921; and U.S. Pat. No. 6,969,597. An exemplary, non-limiting nucleotide sequence encoding DsRed2 is provided in FIG. 11.

Mitochondrial localization signals include a mitochondrial localization signal of human cytomegalovirus protein pUL37$_S$ (see, e.g., U.S. Pat. No. 6,902,885); a mitochondrial localization signal of yUng1p (see, Chatterjee and Singh (2001) *Nucl. Acids Res.* 29:4935-4940); a pseudorabies virus serine/threonine kinase Us3 mitochondrial localization signal (see, Calton et al. (2004) *Virus Genes* 29:131; and a peptide of the sequence: MGVFCLGPWGLGRKLRT-PGKGPLQLLSRLCGDHLQ (SEQ ID NO:25; see, e.g., GenBank Accession No. NP_003353; *Homo sapiens* uracil DNA glycosylase precursor). Other mitochondrial localization signals are known in the art and can be used in the subject invention.

Host Cells

Suitable host cells include mammalian cells, including primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, of particular interest are mammalian cells that normally produce apoE, and cells that normally take up apoE from their environment. Examples of such cells include neuronal cells, microglial cells, and astrocytes. Immortalized neuronal cells, microglial cells, and astrocytes are also of interest. Suitable immortalized cells include, but are not limited to, neuro-2A cells; B103; PC12; NT2; and the like. PC12 cells are available from the American Type Culture Collection (ATCC) as ATCC deposit number CRL-1721. Neuro-2a cells are available from ATCC as ATCC deposit number CCL-131.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOCi (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

Screening Methods

The present invention provides screening methods for identifying agents that reduce apoE-induced impairment of mitochondrial integrity and/or function. The agents so identified are candidate agents for treating an apoE-related disorder.

In some embodiments, the assays are in vitro cell-based screening methods for identifying compounds that reduce apoE-induced impairment of mitochondrial integrity and/or function. In some embodiments, a subject screening assay comprises contacting a eukaryotic cell that produces a toxic apoE polypeptide or a toxic fragment thereof with a test agent; and determining the effect, if any, of the test agent on mitochondrial integrity and/or function. In some embodiments, a subject screening assay comprises contacting a eukaryotic cell with a test agent, which cell comprises a toxic apoE polypeptide or a toxic fragment thereof in the cytosol of the cell; and determining the effect, if any, of the test agent on mitochondrial integrity and/or function. A reduction in apoE-induced impairment of mitochondrial integrity and/or function, compared to mitochondrial integrity and/or function in the absence of the test agent, indicates that the test agent reduces apoE-induced impairment of mitochondrial integrity and/or function. A test agent of interest is an agent that reduces apoE-induced impairment of mitochondrial integrity and/or function by at least about 10%, at least about 15%, at least about 20%, at least about 25%, at least about 30%, at least about 40%, at least about 50%, at least about 60%, at least about 70%, at least about 80%, or at least about 90%, or more, compared to the level of apoE-induced impairment of mitochondrial function in the absence of the test agent.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., from about 50 daltons to about 100 daltons, from about 100 daltons to about 500 daltons, from about 500 daltons to about 1000 daltons, from about 1000 daltons to about 5000 daltons, or from about 5000 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising the test cell) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Screening may be directed to known pharmacologically active compounds and chemical analogs thereof, or to new agents with unknown properties such as those created through rational drug design. Efficacious candidates can be identified by phenotype, i.e. an arrest or reversal of particular cognitive behaviors in a suitable animal model for an apoE-related disorder.

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding.

Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2 H-tetrazolium bromide]) assay, and the like. Agents that do not exhibit significant cytotoxic activity are considered candidate agents.

The cell used in the screening method is in many embodiments one that produces a toxic apoE polypeptide. In other embodiments, the toxic apoE polypeptide is provided exogenously, e.g., the cell is present in a suitable medium, the toxic apoE polypeptide is added to the medium, and the cell takes up the toxic apoE polypeptide from the medium. In many embodiments, the cell is a neuronal cell, and in many embodiments, the cell is a neuronal cell line. Neuronal cell lines are well known in the art, and include, but are not limited to, neuro-2A cells; B103; PC12; NT2; and the like. Suitable neuronal cell lines are listed above. In some embodiments, the cell is a subject host cell.

In some embodiments, a nucleic acid that includes a nucleotide sequence that encodes toxic apoE, as described above, is introduced into the cell, such that the toxic apoE-encoding nucleic acid is transiently or stably expressed in the cell.

In other embodiments, a nucleic acid that includes a nucleotide sequence encoding full-length apoE is introduced into the cell, and the full-length apoE polypeptide that is produced undergoes proteolytic cleavage in the cell to yield a toxic apoE polypeptide in the cytosol.

In other embodiments, the cell is contacted with a toxic apoE polypeptide ("exogenous toxic apoE polypeptide"). The cell takes up the exogenous toxic apoE polypeptide from the medium. To facilitate uptake of exogenous toxic apoE polypeptide, toxic apoE polypeptide can be complexed with a compound that facilitates uptake into eukaryotic cells. Such compounds include, but are not limited to, very low density lipoprotein (VLDL), e.g., β-VLDL; phospholipid/apoE complex; cationic lipids; polyethylene glycol; polylactic-glycolic acid copolymer; dextran; and the like.

In many embodiments, the determining step comprises contacting the cells with an indicator agent that is an indicator of mitochondrial function and/or integrity. Indicator agents will in many embodiments include a fluorescent dye. Suitable indicator agents include, but are not limited to, dihydrorhodamine 123; MitoTracker® mitochondrial function indicator Orange CM-$H_2$ TMRos; MitoTracker® mitochondrial function indicator CMTMRos; MitoTracker® mitochondrial function indicator Red CM-$H_2$XRos; MitoTracker® mitochondrial function indicator Red CMXRos; rhodamine 123; 5,5',6,6'-tetrachloro-1,1',3,3'-tetraethylbenzimidazolylcarbocyanine iodide; tetramethylrhodamine, ethyl ester, perchlorate; and tetramethylrhodamine, methyl ester, perchlorate.

The effect, if any, of the test agent on mitochondrial integrity and/or function is in some embodiments determined by detecting a change in the indicator agent, as described in Example 1.

Real-Time Imaging

In some embodiments, a subject screening assays involve contacting a cell that includes a toxic apoE polypeptide in the cytosol, as described above, and also includes in a mitochondrion a mitochondrial indicator protein the provides a detectable signal. In these embodiments, the effect, if any, of the test agent on mitochondrial integrity and/or function is determined by analyzing the cells by real-time imaging. Real-time imaging can detect, e.g., a change in mitochondrial motility, e.g., as described in Example 2. Proteins that provide for detectable signals are described above. In many embodiments, the mitochondrial indicator protein comprises a mitochondrial localization signal, as described above.

Evaluation In Vivo

A test agent that reduces apoE-induced impairment of mitochondrial function is a candidate agent for treating an apoE4-associated disorder. A candidate agent identified can be further evaluated, in a secondary screen, for efficacy in vivo, using an animal model of an apoE-related disorder. Such secondary screens can employ any phenomena associated learning impairment, dementia or cognitive disorders that can be readily assessed in an animal model. The screening can include assessment of phenomena including, but not limited to: 1) assessment behavioral symptoms associated with memory and learning; and 2) detection of neurodegeneration characterized by progressive and irreversible differentiation of the limbic system, association neocortex, and basal forebrain (neurodegeneration can be measured by, for example, detection of synaptophysin expression in brain tissue) (see, e.g., Games et al. *Nature* 373:523-7 (1995)). These phenomena may be assessed in the screening assays either singly or in any combination.

Generally, the screen will include control values (e.g., the extent of neuronal and/or behavioral deficits in the test animal in the absence of test compound(s)). Test substances which are considered positive, i.e., likely to be beneficial in the treatment of apoE-mediated disorders, will be those which have a substantial effect upon neuronal and behavioral deficits, and associated disorders.

Methods for assessing these phenomena, and the effects expected of a candidate agent for treatment of apoE-associated disorders, are known in the art. For example, methods for using transgenic animals in various screening assays for, for example, testing compounds for an effect on Alzheimer's disease (AD), are found in WO 9640896, published Dec. 19, 1996; WO 9640895, published Dec. 19, 1996; WO 9511994, published May 4, 1995. Examples of assessment of these phenomena are provided below, but are not meant to be limiting.

Behavioral Studies

Behavioral tests designed to assess learning and memory deficits can be employed. An example of such as test is the Morris Water maze (Morris *Learn Motivat* 12:239-260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. *Pharmacol Biochem Behav* 57:257-261 (1997)).

Therapeutic Agents

The present invention provides therapeutic agents that reduce apoE-induced impairment of mitochondrial integrity and/or function; as well as compositions, including pharmaceutical compositions, comprising the agents. In some embodiments, a suitable agent is a peptide that inhibits interaction of a toxic apoE polypeptide with mitochondria. These compositions may include a buffer, which is selected according to the desired use of the agent, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Suitable agents include small organic or inorganic compounds having a molecular weight of more than 50 and less than about 10,000 daltons, e.g., from about 50 daltons to about 100 daltons, from about 100 daltons to about 500 daltons, from about 500 daltons to about 1000 daltons, from about 1000 daltons to about 5000 daltons, or from about 5000 daltons to about 10,000 daltons. Suitable agents may comprise functional groups necessary for structural interaction with proteins, particularly hydrogen bonding, and may include at least an amine, carbonyl, hydroxyl or carboxyl group, and may contain at least two of the functional chemical groups. Suitable agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Suitable agents include, but are not limited to: a peptide comprising an amino acid sequence having at least about 75%, at least about 80%, at least about 85%, at least about 90%, at least about 95%, at least about 98%, at least about 99%, or 100% amino acid sequence identity to a stretch of amino acids 273-299, amino acids 275-299; amino acids 280-299; amino acids 273-295; amino acids 275-295; amino acids 280-299; or amino acids 280-295, of SEQ ID NO:1; where the peptide fragment comprises at least amino acids corresponding to L279, K282, and Q284 of SEQ ID NO:1; and where the peptide has a length of from 15 amino acids to 17 amino acids, from 17 amino acids to 19 amino acids, from 19 amino acids to 21 amino acids, from 21 amino acids to 23 amino acids, from 23 amino acids to 25 amino acids, from 25 amino acids to 27 amino acids, from 27 amino acids to 30 amino acids, from 30 amino acids to 35 amino acids, from 35 amino acids to about 40 amino acids, or from about 40 amino acids to about 50 amino acids. Suitable agents include, but are not limited to: a peptide comprising amino acids 273-299, amino acids 275-299; amino acids 280-299; amino acids 273-295; amino acids 275-295; amino acids 280-299; amino acids 280-295; etc. of an apoE polypeptide, e.g., a fragment comprising amino acids corresponding to amino acids 273-299 of SEQ ID NO:1, where the peptide fragment comprises at least amino acids corresponding to L279, K282, and Q284 of SEQ ID NO:1.

Exemplary, non-limiting peptides include the following:

```
                                            (SEQ ID NO:18)
Gln Arg Gln Trp Ala Gly Leu Val Glu Lys Val Gln
Ala Ala Val Gly Thr Ser Ala Ala Pro Val Pro Ser
Asp Asn His;

(SEQ ID NO:19)
Gln Arg Gln Trp Ala Gly Leu Val Glu Lys Val Gln
Ala Ala Val Gly Thr Ser Ala Ala Pro Val Pro Ser
Asp;

(SEQ ID NO:20)
Gln Arg Gln Trp Ala Gly Leu Val Glu Lys Val Gln
Ala Ala Val Gly Thr Ser Ala Ala Pro Val;

(SEQ ID NO:21)
Ala Gly Leu Val Glu Lys Val Gln Ala Ala Val Gly
Thr Ser Ala Ala Pro Val Pro Ser Asp Asn His;

(SEQ ID NO:22)
Trp Ala Gly Leu Val Glu Lys Val Gln Ala Ala Val
Gly Thr Ser Ala Ala Pro Val Pro Ser Asp Asn;
and (SEQ ID NO:23)
Trp Ala Gly Leu Val Glu Lys Val Gln Ala Ala Val
Gly Thr Ser Ala Ala Pro Val Pro Ser.
```

Peptides can include naturally-occurring and non-naturally occurring amino acids. Peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, peptide may be a cyclic peptide. Peptides may include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics may be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

In some embodiments, the invention provides compositions comprising an agent that reduces apoE-induced impairment of mitochondrial integrity and/or function; and at least one other therapeutic agent. Therapeutic agents that can be formulated together with an agent that reduces apoE-induced impairment of mitochondrial integrity and/or function include, but are not limited to, agents that are used to treat individuals with AD, including, but not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Any known inhibitor of chymotrypsin-like serine proteases can be formulated together with another therapeutic agent used to treat AD. Dosages for each of the above agents are known in the art, and can be used in a pharmaceutical preparation with an agent that reduces apoE-induced impairment of mitochondrial integrity and/or function. For example, Aricept is generally administered at 50 mg orally per day for 6 weeks, and, if well tolerated by the individual, at 10 mg per day thereafter.

Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams, & Wilkins.

The invention provides formulations, including pharmaceutical formulations, comprising an agent that reduces apoE-induced impairment of mitochondrial integrity and/or function. In general, a formulation comprises an effective amount of an agent that reduces apoE-induced impairment of mitochondrial integrity and/or function. An "effective amount" means a dosage sufficient to produce a desired result, e.g., reduction in impairment of mitochondrial motility, reduction in impairment of mitochondrial function, reduction in mitochondrial integrity, an improvement in learning, memory, etc. Generally, the desired result is at least an increase in mitochondrial integrity and/or function as compared to a control. An agent that reduces apoE-induced impairment of mitochondrial integrity and/or function may delivered in such a manner as to avoid the blood-brain barrier, as described in more detail below. An agent that reduces apoE-induced impairment of mitochondrial integrity and/or function may be formulated and/or modified to enable the agent to cross the blood-brain barrier, as described in more detail below.

Formulations

In the subject methods, the active agent(s) may be administered to the host using any convenient means capable of resulting in the desired reduction in impairment of mitochondrial integrity and/or function, reduction in any apoE4-associated neurological disorder, etc.

Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Methods of Treating ApoE-Related Disorders

The present invention provides methods of treating apoE-related disorders in an individual.

The methods generally involve administering to an individual having an apoE-related disorder an effective amount of an agent that reduces apoE-induced impairment of mitochondrial integrity and/or function An "effective amount" of an agent that reduces apoE-induced impairment of mitochondrial integrity and/or function is an amount that reduces apoE-induced impairment of mitochondrial integrity and/or function by at least about 10%, at least about 20%, at least about 30%, at least about 40%, at least about 50%, at least about 60%, at least about 70%, at least about 80% or more, compared to the level of apoE-induced impairment of mitochondrial integrity and/or function in the absence of the agent.

In some embodiments, the invention provides a method of treating Alzheimer's disease. In some embodiments, the method involves administering an agent that reduces apoE-induced impairment of mitochondrial integrity and/or function.

Dosages

Although the dosage used will vary depending on the clinical goals to be achieved, a suitable dosage range is one which provides up to about 1 μg to about 1,000 μg or about 10,000 μg of an agent that reduces apoE-induced impairment of mitochondrial integrity and/or function can be administered in a single dose. Alternatively, a target dosage of an agent that reduces apoE-induced impairment of mitochondrial integrity and/or function can be considered to be about in the range of about 0.1-1000 μM, about 0.5-500 μM, about 1-100 μM, or about 5-50 μM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that reduces apoE-induced impairment of mitochondrial integrity and/or function is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an apoE4-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Crossing the Blood-Brain Barrier

The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the central nervous system (CNS) may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214-219; Baba et al. (1991) *J. Cereb. Blood Flow Metab.* 11:638-643; and Gennuso et al. (1993) *Cancer Invest.* 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682-684; Pardridge (1991) in: *Peptide Drug Delivery to the Brain*; and Kostis et al. (1994) *J. Clin. Pharmacol.* 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, J-cyclodextrin, K-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) *Proc. Natl. Acad. Sci. USA* 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Subjects Suitable for Treatment with a Therapeutic Agent of the Invention

A variety of subjects are suitable for treatment with an agent identified by a method of the invention. Suitable subjects include any individual, particularly a human, who has an apoE-associated disorder, who is at risk for developing an apoE-associated disorder, who has had an apoE-associated disorder and is at risk for recurrence of the apoE-associated disorder, or who is recovering from an apoE-associated disorder.

Such subjects include, but are not limited to, individuals who have been diagnosed as having Alzheimer's disease; individuals who have suffered one or more strokes; individuals who have suffered traumatic head injury; individuals who have high serum cholesterol levels; individuals who have Aβ deposits in brain tissue; individuals who have had one or more cardiac events; subjects undergoing cardiac surgery; and subjects with multiple sclerosis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Effect of apoE Polypeptides on Mitochondrial Integrity and Function

Methods

Reagents. Minimum essential medium (MEM), Opti-MEM, and FBS were from Life Technologies (Rockville, Md.). Polyclonal goat anti-human apoE was from Calbiochem (San Diego, Calif.). Monoclonal antibodies that specifically recognize the lipid binding region of apoE (3H1) were from Karl H. Weisgraber (Gladstone Institutes). Antirabbit, anti-mouse, and anti-goat IgGs coupled to fluorescein or Texas Red were from Vector Laboratories (Burlingame, Calif.). MitoTracker Deep Red 633 was from Invitrogen (Carlsbad, Calif.). A cDNA construct encoding red fluorescent protein fused with a mitochondrial localization signal peptide (DsRed2-Mito) was from BD Biosciences (Mountain View, Calif.).

cDNA Constructs. PCR products encoding wildtype (WT) or N-terminal-truncated apoE4 with its signal peptide were subcloned into a pcDNA 3.1 (+) vector (Invitrogen) containing the cytomegalovirus promoter. A PCR product encoding a signal peptide-green fluorescent protein (GFP)—apoE4 fusion protein was also subcloned into the vector. cDNA constructs encoding apoE4 with various mutations or C-terminal truncations were made from the pcDNA-apoE4 or pcDNA-GFP-apoE4 construct with a QuikChange kit (Stratagene). All constructs were confirmed by sequence analysis.

Cell Culture and Transfection. Mouse neuroblastoma Neuro-2a cells (American Type Culture Collection) maintained at 37° C. in MEM containing 10% FBS were transiently transfected with the apoE4 cDNA constructs using Lipofectamine 2000 (Invitrogen) (25). ApoE4 expression levels were determined by anti-apoE western blotting of cell lysates and media. The truncated and mutated forms of apoE4 that are neurotoxic were expressed at ~15-30% lower levels than full-length apoE4. To exclude their potential weaker antibody response, those forms of apoE4 were tagged with GFP and their expression levels were determined by flow cytometry. Again, their expression levels were ~15-30% lower than those of full-length apoE4. Thus, the results are not due to overexpression.

Immunocytochemistry and Confocal Microscopy. Neuro-2a cells transiently transfected with various apoE4 cDNA constructs were grown in serum-free MEM for 18-24 h, fixed in 3% paraformaldehyde, permeabilized for 45 minutes at room temperature with 500 units of Streptolysis-O (STP-O, Sigma) in BBII buffer (75 mM potassium acetate, 25 mM Hepes, pH 7.2) (for plasma membranes) or 0.5% Tween-20 in PBS (for plasma and intracellular organelle membranes) (51), and stained with polyclonal anti-apoE (1:4000) or monoclonal anti-apoE (3H1, 1:200) and a fluorescein-coupled secondary antibody (Vector Laboratories) (25). Labeled cells were mounted in VectaShield (Vector Laboratories) and viewed with a Radiance 2000-laser-scanning confocal system (Bio-Rad) mounted on an Optiphot-2 microscope (Nikon). Neuro-2a cells transiently transfected with cDNA constructs encoding GFP-apoE4 with mutations or truncations were directly analyzed by confocal microscopy. Some Neuro-2a cells were cotransfected with various apoE cDNA constructs and a construct encoding red fluorescent protein fused with a mitochondrial localization signal peptide (DsRed2-Mito, BD Biosciences), stained with immunofluorescent polyclonal or monoclonal anti-apoE, and analyzed by confocal microscopy.

Cell Survival. Neuro-2a cells grown in 24-well plates were transiently transfected with various apoE4 or GFP-apoE4 cDNA constructs in serum-free Opti-MEM. Cell survival was estimated with an MTT colorimetric assay (52) 48 h after transfection.

Flow Cytometry Analysis of Mitochondrial Function/Integrity. Neuro-2a cells grown in six-well plates were transiently transfected with various GFP-apoE4 cDNA constructs. The culture medium was aspirated 48 h after transfection, and MitoTracker Deep Red 633 (100 nM in MEM containing 10% FBS) was added for 15 min at 37° C. After a wash with serum-free MEM, cells were trypsinized and suspended in 1 ml of PBS, washed twice with PBS by centrifugation (5 min, 1200 rpm), resuspended in 1 ml of PBS, and filtered through a mesh cap into a 5-ml tube. The fluorescence intensity of GFP, which represents apoE4 expression levels, and of MitoTracker Deep Red 633, which represents the levels of mitochondrial function/integrity (53), were analyzed by flow cytometry (BD Biotechnology). Untransfected Neuro-2a cells served as a negative control.

Statistical Analysis. Results are reported as mean±SD. Differences were evaluated by t test or analysis of variance.

Results

The Lipid Binding Region Is Required for ApoE4 Fragment-Related Neurotoxicity. To assess the neurotoxicity of various apoE4 fragments in Neuro-2a cells, an MTT assay was used. Expression of apoE4(1-272) caused 35% greater cell death than full-length apoE4; further carboxyl-terminal truncation to aa240 or 191 to remove the lipid binding region (aa241-272) abolished the neurotoxicity (FIG. 1a). Four mutations of this region (I250A, F257A, W264R, and V269A) that are conserved across different species (54) also abolished the neurotoxicity (FIG. 1b).

Single C-terminal Mutations Make Full-Length ApoE4 Neurotoxic. ApoE4(1-272) was more neurotoxic than full-length apoE4, suggesting that the 27 C-terminal amino acids protect against fragment-related neurotoxicity. Three amino acids in this region (L279, K282, and Q284) are highly conserved in 10 species (54). To assess their importance in this neuroprotective effect, mutations were introduced at each site (L279Q, K282A, or Q284A) into WT apoE4. Each mutation made full-length apoE4 as neurotoxic as apoE4(1-272) (FIG. 1c).

Neurotoxicity Requires Both Lipid and Receptor Binding Regions. To determine if the lipid binding region alone was neurotoxic, Neuro-2a cells expressing only aa241-272 of apoE4 were analyzed. No neurotoxicity was observed (FIG. 1d). To determine which region of the N-terminus was also required for neurotoxicity, cells were transfected with cDNA constructs encoding apoE4(1-272) with progressively longer N-terminal truncations. Neurotoxicity was abolished only by a truncation that removed the receptor binding region (aa135-150) (FIG. 1e).

Positively Charged Amino Acids in the Receptor Binding Region Are Critical for Neurotoxicity. The receptor binding region contains a cluster of positively charged amino acids (arginine and lysine) (1-4). To test their importance in apoE4 fragment-related neurotoxicity, double (K146A and R147A) and triple (R142A, K146A, and R147A) mutations were introduced into apoE4(1-272). The triple mutation abolished the neurotoxic effect of apoE4(1-272), and the double mutation reduced it (FIG. 1f).

FIG. 1. The lipid and receptor binding regions in apoE4 fragments act in concert to cause neurotoxicity as determined with an MTT assay. (a) Survival of cells transfected with WT apoE4, apoE4(1-272), apoE4(1-240), or apoE4(1-191). (b) Survival of cells transfected with WT apoE4, apoE4(1-272), or apoE4(1-272) with four mutations (I250A, F257A, W264R, and V269A). (c) Survival of cells transfected with WT apoE4, apoE4(1-272), or apoE4 with single mutations (L279Q, K282A, or Q284A). (d) Survival of cells transfected with WT apoE4, apoE4(1-272), or apoE(241-272). (e) Survival of cells transfected with WT apoE4, apoE4(1-272), apoE4(87-272), apoE4(127-272), or apoE(171-272). (f) Survival of cells transfected with WT apoE4, apoE4(1-272), or apoE4(1-272) with double (K146A and R147A) or triple (R142A, K146A, and R147A) mutations. Values are mean±SD of 3-6 assays 48 h after transfection. *p<0.05 versus WT apoE4.

ApoE4 Fragments Escape the Secretory Pathway and Interact with Cytoskeletal Components and Mitochondria. To investigate the mechanisms of neurotoxicity, the intracellular localization of full-length or truncated apoE4 in Neuro-2a cells was assessed by immunofluorescence staining. Full-length apoE4 was typically located in the endoplasmic reticulum and Golgi apparatus (FIG. 2a), whereas apoE4(1-272) formed intracellular filamentous inclusions in some cells and had a granular distribution in others (FIG. 2b), suggesting mislocalization of the truncated apoE4 in Neuro-2a cells. Since intracellular filamentous inclusions contain phosphorylated tau and phosphorylated neurofilament proteins, as reported previously (25, 26), some of the fragments must have escaped the secretory pathway and interacted with cytoskeletal components. In cells expressing both apoE4(1-272) and DsRed2-Mito, the granule-associated apoE4 fragments were in the mitochondria (FIG. 2c).

Figure 2:
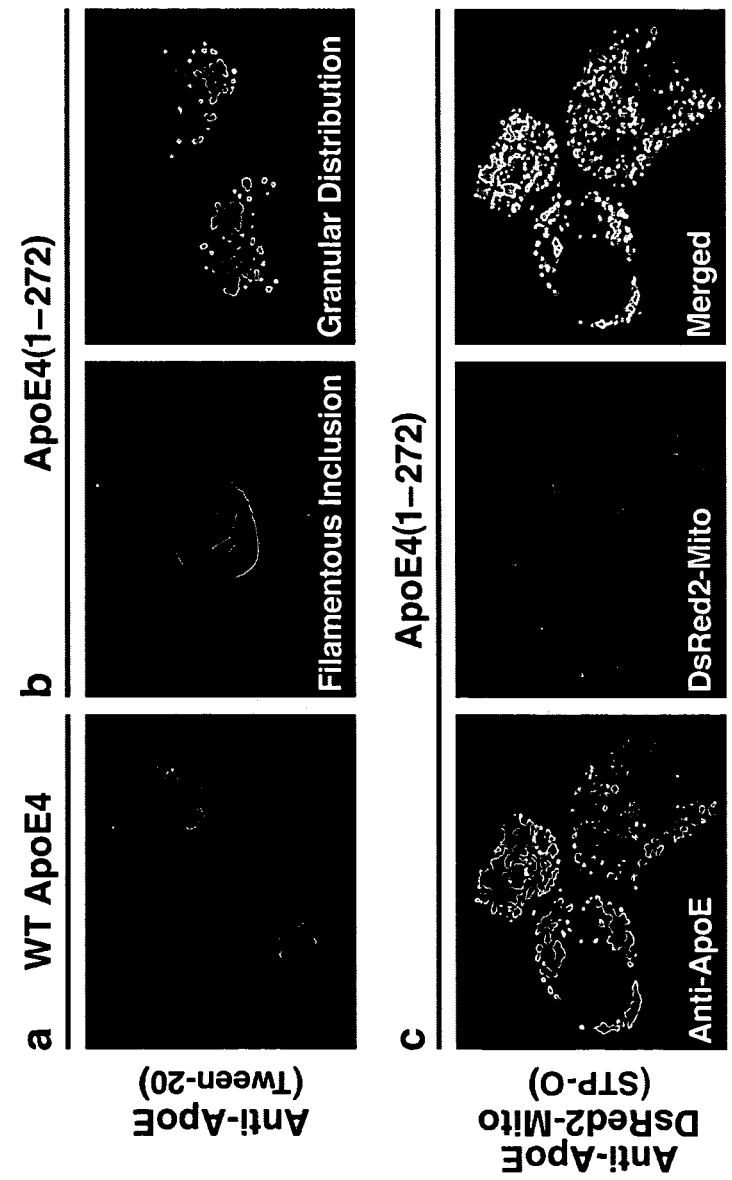
FIGS. 2A-C depict the intracellular distribution of various forms of apoE4.

FIG. 2. Intracellular distribution of various forms of apoE4 as determined by immunocytochemistry and confocal microscopy. (a) Cells transfected with WT apoE4, permeabilized with Tween-20, and stained with anti-apoE (green in original; shown as bright in black-and-white image). (b) Cells transfected with apoE4(1-272), permeabilized with Tween-20, and stained with anti-apoE (green in original; shown as bright in black-and-white image). (c) Cells co-transfected with apoE4(1-272) and DsRed2-Mito (red in original; shown as bright in black-and-white image), permeabilized with STP-O, and stained with anti-apoE (yellow in original; shown as bright in black-and-white image). The merged image indicates co-localization of apoE4(1-272) with mitochondria.

Mitochondrial Mislocalization Requires the Lipid and Receptor Binding Regions. The intracellular location of apoE (171-272), containing only the lipid binding region, and apoE4(1-240), containing only the receptor binding region, was investigated. Neither was located in the mitochondria, and their intracellular distributions were similar to that of full-length apoE4 (FIG. 3a-f). The mitochondrial mislocalization was also abolished by the quadruple mutation in the lipid binding region [E4(1-272)-AARA] and the triple mutations in the receptor binding region [E4(1-272)-3A] (FIG. 3g-j).

Figure 3:
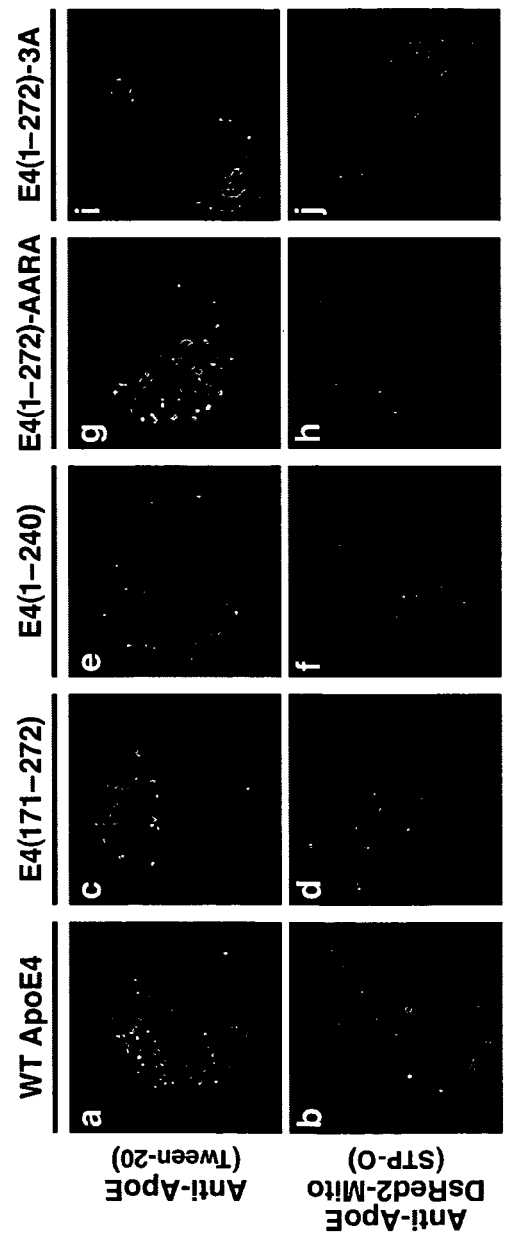
FIGS. 3A-J depict mitochondrial mislocalization of apoE4 fragments.

FIG. 3. The lipid and receptor binding regions act in concert to cause mitochondrial mislocalization of apoE4 fragments. Cells transfected with WT apoE4 (a), apoE(171-272) (c), apoE4(1-240) (e), apoE4(1-272)-AARA with four mutations (I250A, F257A, W264R, and V269A) in the lipid binding region (g), or apoE4(1-272)-3A with three mutations (R142A, K145A, and R146A) in the receptor binding region (i) were permeabilized with 0.5% Tween-20 (a, c, e, g, and I) and stained with anti-apoE (green in original; shown as bright in black-and-white image). Cells cotransfected with DsRed2-Mito (red in original; shown as bright in black-and-white image) and various apoE4 constructs mentioned above were permeabilized with 500 units STP-O (b, d, f h, andj) and stained with anti-apoE (green in original; shown as bright in black-and-white image). The cells were then analyzed by confocal microscopy for only green (a, c, e, g, and i) or both red and green (b, d, f h, and j).

The Receptor Binding Region Is Required to Escape the Secretory Pathway, and the Lipid Binding Region Mediates Mitochondrial Interaction. To dissect the functions of the lipid and receptor binding regions, the effect of removing the N-terminal secretion signal peptide from fragments containing only one of the two regions was assessed. When expressed directly in the cytosol, apoE(171-272), containing only the lipid binding region, interacted with the mitochondria (FIGS. 4a and 4b), although the same fragment with the signal peptide was retained in the secretory pathway and did not interact with the mitochondria (FIG. 3c and 3d). Furthermore, triple mutation of the receptor binding region caused apoE4(1-272) with the signal peptide to be retained in the secretory pathway and, thus, no interaction with the mitochondria (FIG. 3i and 3j). ApoE4(1-191), containing only the receptor binding region, did not interact with the mitochondria, even when expressed directly in the cytosol (FIG. 4c and 4d).

Figure 4:
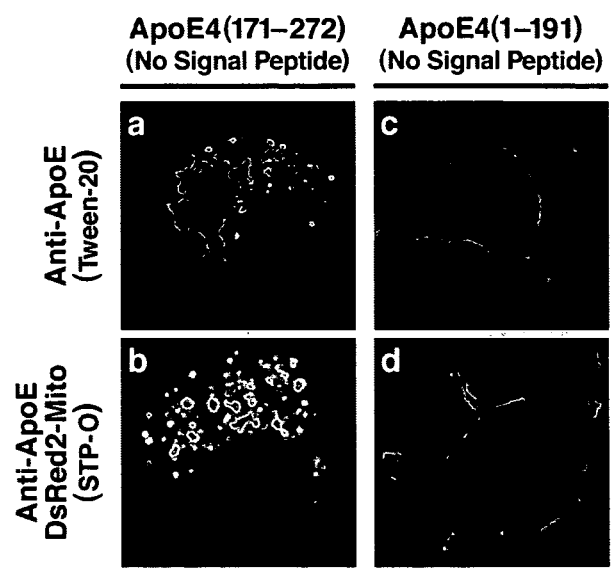
FIGS. 4A-D depict the effect of the receptor binding region on the interaction of apoE polypeptides with mitochondria.

FIG. 4. The receptor binding region is required to escape the secretory pathway and the lipid binding region mediates mitochondria interaction. Cells transfected with apoE(171-272) without signal peptide (a) or apoE4(1-191) without signal peptide (c) were permeabilized with 0.5% Tween-20 and stained with anti-apoE (green in original; shown as bright in black-and-white image). Cells cotransfected with DsRed2-Mito (red) and either of those two apoE4 constructs were permeabilized with 500 units STP-O (b and d) and stained with anti-apoE (green in original; shown as bright in black-and-white image). The cells were analyzed as described above.

Figure 5:
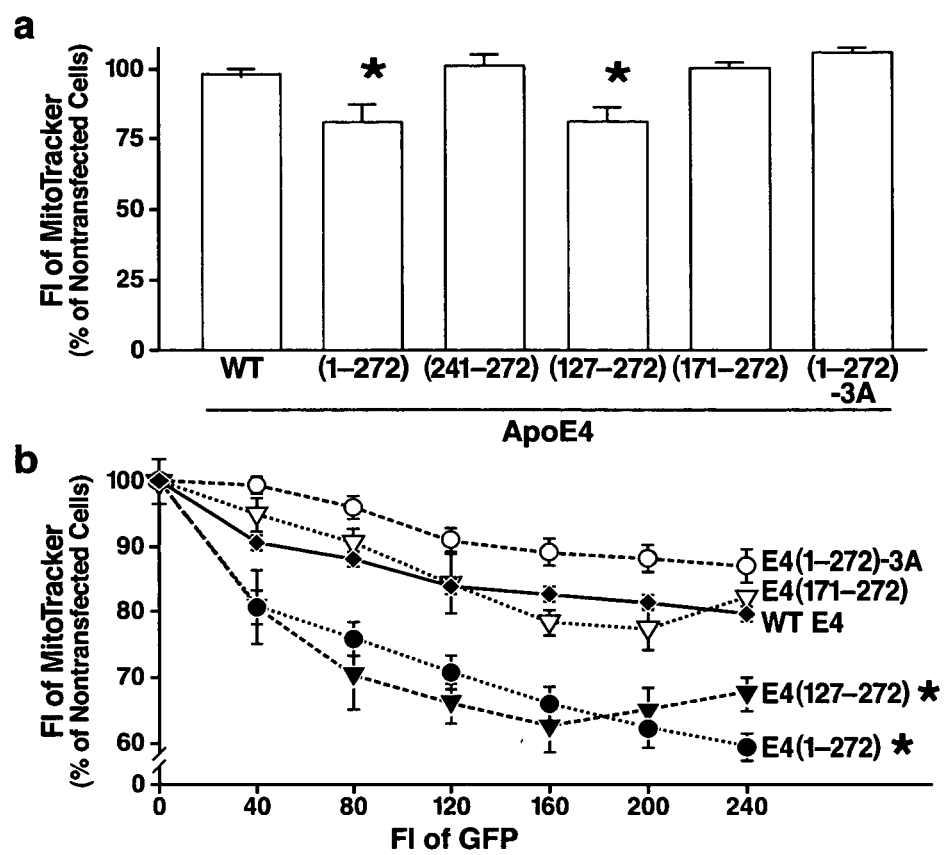
FIGS. 5A and 5B depict the effect of lipid binding region and receptor binding region on mitochondrial dysfunction.

The Lipid and Receptor Binding Regions Together Impair Mitochondrial Function/Integrity. To investigate the effect of apoE4 fragments on mitochondria, Neuro-2a cells transfected with various apoE4 constructs were incubated with MitoTracker Deep Red 633, and fluorescence intensity was analyzed by flow cytometry as a measure of mitochondrial function/integrity (53) (FIG. 5). Fluorescence intensity was 25% lower in cells expressing apoE4(1-272) or apoE(127-272) than in those expressing full-length apoE4 (FIG. 5A). Since only functional mitochondria with a normal membrane potential can effectively take up and store MitoTracker Deep Red 633, this finding suggests that only apoE4 fragments with both the lipid and receptor binding regions can impair mitochondrial function/integrity. Importantly, this effect was dependent on the level of expression (FIG. 5B). Consistent with the immunocytochemical data, apoE4 fragments containing only one of the two regions and those with the quadruple mutation in the lipid binding region or the triple mutation in the receptor binding region had no significant effect on mitochondrial function/integrity (FIG. 5).

FIG. 5. The lipid and receptor binding regions in apoE4 fragments act in concert to cause mitochondrial dysfunction as determined by MitoTracker Deep Red 633 staining and flow cytometry. (a) Effects of various forms of apoE4, expressed at similar levels, on mitochondrial function/integrity. (b) Effect on mitochondrial function/integrity is dependent on expression levels of apoE4 fragments, as measured by fluorescence intensity (FI) of GFP. Values are mean±SD of 3-6 assays. *p<0.05 versus WT apoE4, E4(171-272), and E4(1-272)-3A. E4(1-272)-3A, apoE4(1-272) with a triple mutation in the receptor binding region.

Example 2

Time-lapse recording of mitochondrial motility in differentiated PC12 cells. PC12 cells (FIG. 8A) were differentiated with nerve growth factor (NGF, 40 ng/ml), transfected 7 days later with dsRed2-Mito, and differentiated for additional 3-7 days to allow further neurite outgrowth (FIG. 8B). Time-lapse fluorescence images of mitochondria in neurites of 10-15-day-differentiated PC12 cells expressing dsRed2-Mito (FIG. 8C) were recorded at room temperature for 15 min at 12 frames per min. To quantify mitochondrial motility, image-sequences were analyzed with NIH ImageJ software (FIGS. 8D and E). As control, mitochondria from differentiated PC12 cells were analyzed.

Figure 8:
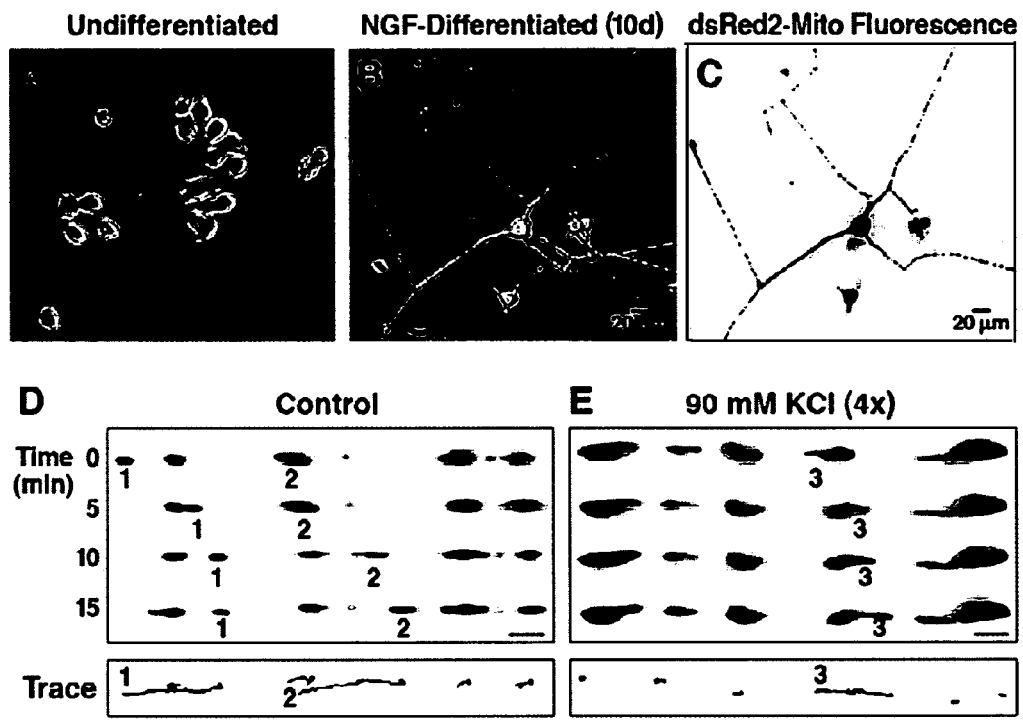
FIGS. 8A-E depict undifferentiated and differentiated PC12 cells and time-elapse recordings of mitochondria in their neurites.

FIG. 8. Undifferentiated and differentiated PC12 cells and time-lapse recordings of mitochondria in their neurites. Phase-contrast micrograph of undifferentiated PC12 cells (A) and after 10 days differentiation with 40 ng/ml NGF (B). (C) Fluorescence micrograph (inverted signal) of dsRed2-Mito, representing mitochondria. (D and E) Time-lapse recordings of mitochondria in neurites of PC12 cells. Numbers indicate moving mitochondria under control conditions (1 and 2 in D) and after repetitive depolarizations (3 in E). The bottom trace in D and E summarizes the movement of individual mitochondria.

As reported for primary hippocampal neurons, ~23% of the mitochondria were moving, and ~77% remained stationary (FIG. 9A).

To assess motility responses to neuronal activity, cells were repetitively depolarized with KCl (90 mM, 4×3 min, separated by 4×10-min wash) (42, 94). The percentage of moving mitochondria was reduced by 44% (FIG. 9A). Both the net moving distance and the average moving velocity (moving distance/15 min) in the anterograde direction (toward the growth cone) were drastically reduced (FIGS. 9B and 9C). No significant changes were seen in retrograde motility (toward the soma). Since most mitochondria did not move constantly, the average velocity might not reflect the true moving speed. Therefore, the moving velocity was also calculated (moving distance/the time when mitochondria were moving). Mitochondrial moving velocity was unaltered (FIG. 9D).

To assess mitochondrial morphology and distribution, a mitochondrial index (added mitochondrial length in a given neurite/neurite length) was determined. Depolarizations reduced the mitochondrial index by 22.5%, probably reflecting redistribution toward areas of high-energy demand, due to the calcium dependent engagement or disengagement of molecular motors (dynein and kinesin).

In contrast, inhibition of neuronal activity by tetrodotoxin (TTX, 1 µM) increased mitochondrial dynamics (FIG. 9A-D), without affecting the mitochondrial index. Thus, our time-lapse recording approach is well established and validated as described above.

Figure 9:
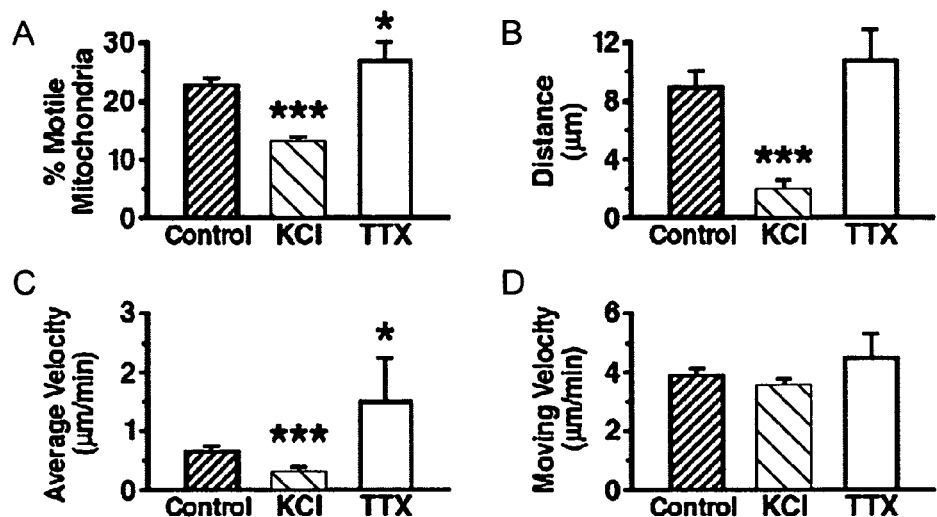
FIGS. 9A-D depict activity-dependent changes in mitochondrial motility.

FIG. 9. Activity-dependent changes in mitochondrial motility. (A) Percentage of moving mitochondria in various conditions. (B) Net moving distance of mitochondria in 15 min [(anterograde distance−retrograde distance)/n] (C) Average anterograde velocity (anterograde moving distance/15 min.) (D) Anterograde moving velocity (anterograde moving distance/time spent moving). In A-D, 198 mitochondria from 14 cells and 126 mitochondria from eight cells in two independent experiments were analyzed for control and KCl depolarization respectively; for TTX (1 µM, 1 h preincubation), 38 mitochondria from four cells in one experiment were analyzed. Values are mean±SEM. *p<0.05, ***p<0.001 vs. control (t test).

Effects of exogenous apoE isoforms and apoE4 fragment on mitochondrial motility. Both apoE4 and apoE4(1-272) (7.5 µg/ml of culture medium, 24 h incubation) significantly decreased the percentage of moving mitochondria, their net moving distance and average velocity in the anterograde direction (FIGS. 10A-C), but not retrograde direction. ApoE4 (1-272) also reduced the moving velocity (FIG. 10D), suggesting that the fragment impairs the function of molecular motors and/or the cytoskeletal track. In contrast, mitochondrial motility was not affected by exogenous apoE3 (FIG. 8A-D), probably reflecting isoform-specific differences in regulating calcium influx (10). Furthermore, apoE4 and apoE4(1-272) significantly reduced the average mitochondrial length; apoE3 did not (FIG. 10E). Finally, the apoE isoforms significantly decreased the mitochondrial index (apoE4(1-272)>apoE4>apoE3) (FIG. 10F).

Figure 10:
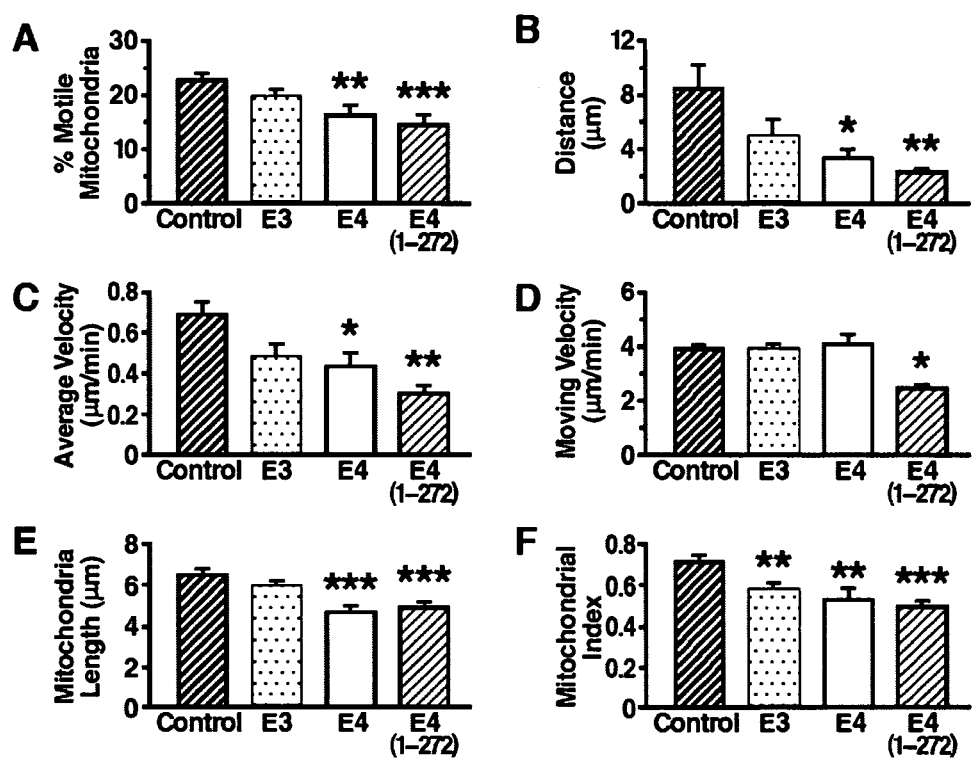
FIGS. 10A-F depict effects of apoE isoforms and the apoE4 fragment on mitochondrial motility and morphology.

FIG. 10. Effects of apoE isoforms and the apoE4 fragment on mitochondrial motility and morphology. Differentiated PC12 cells were incubated for 24 h at 37° C. with 7.5 µg/ml of apoE isoforms or apoE4(1-272) fragment. Mitochondrial dynamics were analyzed as percentage of moving mitochondria (A), net distance traveled in 15 min (B), average anterograde velocity (C), anterograde moving velocity (D), average mitochondrial length (E), and mitochondrial index (F). Data in A-F are from two independent experiments. In A-D, control, n=198 from 14 cells; apoE3, n=159 from nine cells; apoE4, n=52 from four cells; and apoE4(1-272), n=101 from six cells. In E-F, control, n=229 from 10 cells; apoE3, n=326 from 10 cells; apoE4, n=214 from 6 cells, and apoE4(1-272), n=304 from 11 cells. Values are mean±SEM. *p<0.05, p<0.01, *p<0.001 vs. control (t test).

References

1. Mahley, R. W. (1988) *Science* 240, 622-630.
2. Mahley, R. W. & Huang, Y. (1999) *Curr. Opin. Lipidol.* 10, 207-217.
3. Huang, Y. & Mahley, R. W. (1999) in *Plasma Lipids and Their Role in Disease*, eds. Barter, P. J. & Rye, K.-A. (Harwood Academic Publishers, Amsterdam), pp. 257-284.
4. Mahley, R. W. & Rall, S. C., Jr. (2000) *Annu. Rev. Genomics Hum. Genet.* 1, 507-537.
5. Strittmatter, W. J., Saunders, A. M., Schmechel, D., Pericak-Vance, M., Enghild, J., Salvesen, G. S. & Roses, A. D. (1993) *Proc. Natl. Acad. Sci. U.S.A.* 90, 1977-1981.
6. Roses, A. D. (1994) *J. Neuropathol. Exp. Neurol.* 53, 429-437.
7. Corder, E. H., Saunders, A. M., Strittmatter, W. J., Schmechel, D. E., Gaskell, P. C., Small, G. W., Roses, A. D., Haines, J. L. & Pericak-Vance, M. A. (1993) *Science* 261, 921-923.
8. Farrer, L. A., Cupples, L. A., Haines, J. L., Hyman, B., Kukull, W. A., Mayeux, R., Myers, R. H., Pericak-Vance, M. A., Risch, N. & Van Duijn, C. M. (1997) *J. Am. Med. Assoc.* 278, 1349-1356.
9. Strittmatter, W. J., Weisgraber, K. H., Huang, D. Y., Dong, L.-M., Salvesen, G. S., Pericak-Vance, M., Schmechel, D., Saunders, A. M., Goldgaber, D. & Roses, A. D. (1993) *Proc. Natl. Acad. Sci. U.S.A.* 90, 8098-8102.
10. Ma, J., Yee, A., Brewer, H. B., Jr., Das, S. & Potter, H. (1994) *Nature* 372, 92-94.
11. Wisniewski, T., Castaño, E. M., Golabek, A., Vogel, T. & Frangione, B. (1994) *Am. J. Pathol.* 145, 1030-1035.
12. LaDu, M. J., Falduto, M. T., Manelli, A. M., Reardon, C. A., Getz, G. S. & Frail, D. E. (1994) *J. Biol Chem.* 269, 23403-23406.
13. Holtzman, D. M., Bales, K. R., Tenkova, T., Fagan, A. M., Parsadanian, M., Sartorius, L. J., Mackey, B., Olney, J., McKeel, D., Wozniak, D. & Paul, S. M. (2000) *Proc. Natl. Acad. Sci. U.S. A.* 97, 2892-2897.
14. Bales, K. R., Verina, T., Cummins, D. J., Du, Y., Dodel, R. C., Saura, J., Fishman, C. E., DeLong, C. A., Piccardo, P., Petegnief, V., Ghetti, B. & Paul, S. M. (1999) *Proc. Natl. Acad. Sci. U.S.A.* 96, 15233-15238.
15. Irizarry, M. C., Cheung, B. S., Rebeck, G. W., Paul, S. M., Bales, K. R. & Hyman, B. T. (2000) *Acta. Neuropathol.* 100, 451-458.

16. Buttini, M., Yu, G.-Q., Shockley, K., Huang, Y., Jones, B., Masliah, E., Mallory, M., Yeo, T., Longo, F. M. & Mucke, L. (2002) *J. Neurosci.* 22, 10539-10548.
17. Buttini, M., Orth, M., Bellosta, S., Akeefe, H., Pitas, R. E., Wyss-Coray, T., Mucke, L. & Mahley, R. W. (1999) *J. Neurosci.* 19, 4867-4880.
18. Miyata, M. & Smith, J. D. (1996) *Nat. Genet.* 14, 55-61.
19. Gibson, G. E., Haroutunian, V., Zhang, H., Park, L. C. H., Shi, Q., Lesser, M., Mohs, R. C., Sheu, R. K.-F. & Blass, J. P. (2000) *Ann. Neurol.* 48, 297-303.
20. Ohta, S., Ohsawa, I., Kamino, K., Ando, F. & Shimokata, H. (2004) *Ann. N.Y. Acad. Sci.* 1011, 36-44.
21. Kamino, K., Nagasaka, K., Imagawa, M., Yamamoto, H., Yoneda, H., Ueki, A., Kitamura, S., Namekata, K., Miki, T. & Ohta, S. (2000) *Biochem. Biophys. Res. Commun.* 273, 192-196.
22. Herz, J. & Beffert, U. (2000) *Nat. Rev. Neurosci.* 1, 51-58.
23. Strittmatter, W. J., Saunders, A. M., Goedert, M., Weisgraber, K. H., Dong, L.-M., Jakes, R., Huang, D. Y., Pericak-Vance, M., Schmechel, D. & Roses, A. D. (1994) *Proc. Natl. Acad. Sci. U. S. A.* 91, 11183-11186.
24. Tesseur, I., Van Dorpe, J., Spittaels, K., Van den Haute, C., Moechars, D. & Van Leuven, F. (2000) *Am. J. PathoL* 156, 951-964.
25. Huang, Y., Liu, X. Q., Wyss-Coray, T., Brecht, W. J., Sanan, D. A. & Mahley, R. W. (2001) *Proc. Natl. Acad. Sci. U.S.A.* 98, 8838-8843.
26. Ljungberg, M. C., Dayanandan, R., Asuni, A., Rupniak, T. H., Anderton, B. H. & Lovestone, S. (2002) *Neuroreport* 13, 867-870.
27. Harris, F. M., Brecht, W. J., Xu, Q., Tesseur, I., Kekonius, L., Wyss-Coray, T., Fish, J. D., Masliah, E., Hopkins, P. C., Scearce-Levie, K., Weisgraber, K. H., Mucke, L., Mahley, R. W. & Huang, Y. (2003) *Proc. Natl. Acad. Sci. U.S.A.* 100, 10966-10971.
28. Brecht, W. J., Harris, F. M., Chang, S., Tesseur, I., Yu, G.-Q., Xu, Q., Fish, J. D., Wyss-Coray, T., Buttini, M., Mucke, L., Mahley, R. W. & Huang, Y. (2004) *J. Neurosci.* 24, 2527-2534.
29. Raber, J., Wong, D., Buttini, M., Orth, M., Bellosta, S., Pitas, R. E., Mahley, R. W. & Mucke, L. (1998) *Proc. Natl. Acad. Sci. U.S.A.* 95, 10914-10919.
30. Raber, J., Bongers, G., LeFevour, A., Buttini, M. & Mucke, L. (2002) *J. Neurosci.* 22, 5204-5209.
31. Ji, Z.-S., Miranda, R. D., Newhouse, Y. M., Weisgraber, K. H., Huang, Y. & Mahley, R. W. (2002) *J. Biol. Chem.* 277, 21821-21828.
32. Cataldo, A. M., Barnett, J. L., Pieroni, C. & Nixon, R. A. (1997) *J. Neurosci.* 17, 6142-6151.
33. Cataldo, A. M., Peterhoff, C. M., Troncoso, J. C., Gomez-Isla, T., Hyman, B. T. & Nixon, R. A. (2000) *Am. J. Pathol.* 157, 277-286.
34. Grbovic, O. M., Mathews, P. M., Jiang, Y., Schmidt, S. D., Dinakar, R., Summers-Terio, N. B., Ceresa, B. P., Nixon, R. A. & Cataldo, A. M. (2003) *J. Biol. Chem.* 278, 31261-31268.
35. Beffert, U. & Poirier, J. (1996) *Ann. N.Y. Acad. Sci.* 777, 166-174.
36. Beisiegel, U., Schneider, W. J., Goldstein, J. L., Anderson, R. G. W. & Brown, M. S. (1981) *J. Biol. Chem.* 256, 11923-11931.
37. Diedrich, J. F., Minnigan, H., Carp, R. I., Whitaker, J. N., Race, R., Frey, W., II & Haase, A. T. (1991) *J. Virol.* 65, 4759-4768.
38. Han, S.-H., Einstein, G., Weisgraber, K. H., Strittmatter, W. J., Saunders, A. M., Pericak-Vance, M., Roses, A. D. & Schmechel, D. E. (1994) *J. Neuropathol. Exp. Neurol.* 53, 535-544.
39. Bao, F., Arai, H., Matsushita, S., Higuchi, S. & Sasaki, H. (1996) *Neuroreport* 7, 1733-1739.
40. Metzger, R. E., LaDu, M. J., Pan, J. B., Getz, G. S., Frail, D. E. & Falduto, M. T. (1996) *J. Neuropathol. Exp. Neurol.* 55, 372-380.
41. Xu, P.-T., Schmechel, D., Qiu, H.-L., Herbstreith, M., Rothrock-Christian, T., Eyster, M., Roses, A. D. & Gilbert, J. R. (1999) *Neurobiol. Dis.* 6, 63-75.
42. Xu, P.-T., Gilbert, J. R., Qiu, H.-L., Ervin, J., Rothrock-Christian, T. R., Hulette, C. & Schmechel, D. E. (1999) *Am. J. Pathol.* 154, 601-611.
43. Xu, P.-T., Gilbert, J. R., Qiu, H.-L., Rothrock-Christian, T., Settles, D. L., Roses, A. D. & Schmechel, D. E. (1998) *Neurosci. Lett.* 246, 65-68.
44. Xu, P.-T., Schmechel, D., Rothrock-Christian, T., Burkhart, D. S., Qiu, H.-L., Popko, B., Sullivan, P., Maeda, N., Saunders, A. M., Roses, A. D. & Gilbert, J. R. (1996) *Neurobiol. Dis.* 3, 229-245.
45. Aoki, K., Uchihara, T., Sanjo, N., Nakamura, A., Ikeda, K., Tsuchiya, K. & Wakayama, Y. (2003) *Stroke* 34, 875-880.
46. Dupont-Wallois, L., Soulié, C., Sergeant, N., Wavrant-de Wrieze, N., Chartier-Harlin, M.-C., Delacourte, A. & Caillet-Boudin, M.-L. (1997) *Neurobiol. Dis.* 4, 356-364.
47. Ferreira, S., Dupire, M.-J., Delacourte, A., Najib, J. & Caillet-Boudin, M.-L. (2000) *Exp. Neurol.* 166, 415-421.
48. Harris, F. M., Tesseur, I., Brecht, W. J., Xu, Q., Mullendorff, K., Chang, S., Wyss-Coray, T., Mahley, R. W. & Huang, Y. (2004) *J. Biol. Chem.* 279, 3862-3868.
49. Huang, Y., Weisgraber, K. H., Mucke, L. & Mahley, R. W. (2004) *J. Mol. Neurosci.* 23, 189-204.
50. Narayanaswami, V. & Ryan, R. O. (2000) *Biochim. Biophys. Acta* 1483, 15-36.
51. Du, X., Stoops, J. D., Mertz, J. R., Stanley, C. M. & Dixon, J. L. (1998) *J. Cell Biol.* 141, 585-599.
52. Berridge, M. V. & Tan, A. S. (1993) *Arch. Biochem. Biophys.* 303, 474-482.
53. Kalbacova, M., Vrbacky, M., Drahota, Z. & Melková, Z. (2003) *Cytometry* 52A, 110-116.
54. Weisgraber, K. H. (1994) *Adv. Protein Chem.* 45, 249-302.
55. Tolar, M., Marques, M. A., Harmony, J. A. K. & Crutcher, K. A. (1997) *J. Neurosci.* 17, 5678-5686.
56. Tolar, M., Keller, J. N., Chan, S., Mattson, M. P., Marques, M. A. & Crutcher, K. A. (1999) *J. Neurosci.* 19, 7100-7110.
57. Frankel, A. D. & Pabo, C. O. (1988) *Cell* 55, 1189-1193.
58. Green, M. & Loewenstein, P. M. (1988) *Cell* 55, 1179-1188.
59. Schwarze, S. R., Ho, A., Vocero-Akbani, A. & Dowdy, S. F. (1999) *Science* 285, 1569-1572.
60. Cao, G., Pei, W., Ge, H., Liang, Q., Luo, Y., Sharp, F. R., Lu, A., Ran, R., Graham, S. H. & Chen, J. (2002) *J. Neurosci.* 22, 5423-5431.
61. Fawell, S., Seery, J., Daikh, Y., Moore, C., Chen, L. L., Pepinsky, B. & Barsoum, J. (1994) *Proc. Natl. Acad. Sci. U.S.A.* 91, 664-668.
62. Miura, S.-I., Okamoto, T., Via, D. P. & Saku, K. (2002) *Circ. J.* 66, 1054-1056.
63. Liu, K., Ou, J., Saku, K., Jimi, S., Via, D. P., Sparrow, J. T., Zhang, B., Pownall, H. J., Smith, L. C. & Arakawa, K. (1999) *Arterioscler. Thromb. Vasc. Biol.* 19, 2207-2213.
64. Cho, H. S., Hyman, B. T., Greenberg, S. M. & Rebeck, G. W. (2001) *J. Neuropathol. Exp. Neurol.* 60, 342-349.

65. Ghosh, S. S., Swerdlow, R. H., Miller, S. W., Sheeman, B., Parker, W. D., Jr. & Davis, R. E. (1999) *Ann. N.Y. Acad. Sci.* 893, 176-191.
66. Trimmer, P. A., Swerdlow, R. H., Parks, J. K., Keeney, P., Bennett, J. P., Jr., Miller, S. W., Davis, R. E. & Parker, W. D., Jr. (2000) *Exp. Neurol.* 162, 37-50.
67. Hirai, K., Aliev, G., Nunomura, A., Fujioka, H., Russell, R. L., Atwood, C. S., Johnson, A. B., Kress, Y., Vinters, H. V., Tabaton, M., Shimohama, S., Cash, A. D., Siedlak, S. L., Harris, P. L. R., Jones, P. K., Petersen, R. B., Perry, G. & Smith, M. A. (2001) *J. Neurosci.* 21, 3017-3023.
68. Small, G. W., Mazziotta, J. C., Collins, M. T., Baxter, L. R., Phelps, M. E., Mandelkern, M. A., Kaplan, A., La Rue, A., Adamson, C. F. & Chang, L. (1995) *J. Am. Med. Assoc.* 273, 942-947.
69. Small, G. W., Ercoli, L. M., Silverman, D. H. S., Huang, S.-C., Komo, S., Bookheimer, S. Y., Lavretsky, H., Miller, K., Siddarth, P., Rasgon, N. L., Mazziotta, J. C., Saxena, S., Wu, H. M., Mega, M. S., Cummings, J. L., Saunders, A. M., Pericak-Vance, M. A., Roses, A. D., Barrio, J. R. & Phelps, M. E. (2000) *Proc. Natl Acad. Sci. U. S. A.* 97, 6037-6042.
70. Reiman, E. M., Caselli, R. J., Chen, K., Alexander, G. E., Bandy, D. & Frost, J. (2001) *Proc. Natl. Acad. Sci. U.S.A.* 98, 3334-3339.
71. Reiman, E. M., Chen, K., Alexander, G. E., Caselli, R. J., Bandy, D., Osborne, D., Saunders, A. M. & Hardy, J. (2004) *Proc. Natl. Acad. Sci. U.S.A.* 101, 284-289.

Example 3

Neuronal Activity-Dependent Impairment of Mitochondrial Dynamics and Synaptogenesis by Apolipoprotein E4 and its Fragment in Neuronal Cultures Methods Reagents. TTX and NGF were from Alomone Labs (Jerusalem, Israel). AP5 was from Tocris Bioscience (Ellisville, Mo.). Nimodipine and all other chemicals were from Sigma (St. Louis, Mo.). Recombinant apoE3 and apoE4 were kindly provided by Dr. Karl Weisgraber (Gladstone Institutes, San Francisco, Calif.). The mitochondrial marker pCMV-DsRed2-Mito carrying the mitochondrial targeting sequence of cytochrome c was from Clontech (Mountain View, Calif.). The pPDGF-EGFP-β-actin construct (Morales 2001) was a generous gift of Dr. Yukiko Goda (University College London, London, UK). All plasmids were purified with the Plasmid Maxi Kit from Qiagen (Valencia, Calif.).

Cell culture and transfection. PC12 cells were maintained in Dulbecco's modified Eagle's medium supplemented with 5% horse serum, 2.5% fetal calf serum, and 1 mM L-glutamine (all from Invitrogen, Carlsbad, Calif.). PC12 cells were plated 30-mm glass coverslips ($25 \times 10^4$ cells) coated with poly-L-lysine, differentiated in regular growth medium with 2.5% horse serum supplemented with 40 ng/ml NGF, and used for experiments 3-8 days after transfection.

Cortices or hippocampi from neonatal rat pups were dissected and treated with papain (10 units ml$^{-1}$, 30 min; Worthington Biochemical, Lakewood, N.J.) and the with trypsin inhibitor (10 mg ml$^{-1}$, 15 min). Dissociated neurons were plated on 12-mm glass coverslips (Fisher Scientific, Hampton, N.H.) ($8 \times 10^5$ cells per cm$^2$) coated with poly-L-lysine. After 2 h, cells were transferred into Neurobasal medium supplemented with B27, 1 mM L-glutamine, and 100 µg/ml penicillin/streptomycin (Invitrogen). Neurons were routinely transfected after 10 days in culture and used for experiments 5-7 days after transfection. Cells were maintained in a humidified incubator with 5% $CO_2$ at 37° C.

Differentiated PC12 cells and primary neurons were transfected with dsRed2-Mito construct or cotransfected with dsRed2-Mito and pPDGF-EGFP-β-actin constructs using Lipofectamine 2000 (Invitrogen). DNA (2 µg) together with 3 µl of Lipofectamine 2000 was routinely used for transfection and cotransfection.

Generation of apoE cell lines. PC12 Tet-on cells (Clontech, Mountain View, Calif.) were cotransfected with pTRE constructs encoding various forms of apoE (generated at Gladstone) and a puromycin selection marker construct (Clontech). ApoE expression levels were quantified by anti-apoE western blotting and found to be comparable.

Neuronal activation and inhibition. For neuronal activation, differentiated PC12 cells or primary neurons were depolarized four times for 3 min each with KCl (90 mM) and separated by 10-min washes in the presence or absence of various forms of apoE. For neuronal inhibition, differentiated PC12 cells or primary neurons were incubated with 1 µM of TTX for 4-24 hours in the presence or absence of various forms of apoE (Li et al. (2004) *Cell*) 119:873).

Confocal Microscopy. Cultured primary neurons treated with various forms of apoE were fixed for 20 min in ice-cold 4% paraformaldehyde in PBS and mounted with Vectashield (Vector Laboratories Burlingame, Calif.). Digital images of EGFP and dsRed fluorescence in primary neurons were collected on a laser-scanning confocal microscope with a Bio-Rad Radiance 2000 scanhead (Bio-Rad, Hercules, Calif.) mounted on a BX60 microscope (Olympus, Melville, N.Y.) with a 60× oil objective.

Time-lapsefluorescent microscopy. Digital images of dsRed fluorescence in neurites of PC12 cells differentiated with NGF for 13-16 days were captured at 12 frames/min for 15 min with a Orca II cooled CCD camera (Hamamatsu, Bridgewater, N.J.) mounted on a Nikon Eclipse TE300 microscope (Melville, N.Y.) equipped with a 40× air objective and a uniblitz electronic shutter (Vincent Associates, Rochester, N.Y.). During recordings, cells were kept at room temperature in $CO_2$-independent medium (Invitrogen) supplemented with 1 mM L-glutamine, 2.5% fetal calf serum, and 2.5% horse serum.

Image analysis. Images were analyzed with NIH ImageJ software (available on the internet at rsb.info.nih.gov/ij/). The manual tracker plug-in was used to track and analyze mitochondrial movement.

Statistical Analysis. The t test was used for statistical analyses.

Results

ApoE4 and its Fragment Reduce the Dendritic Spine Density in Primary Neurons

Figure 12:
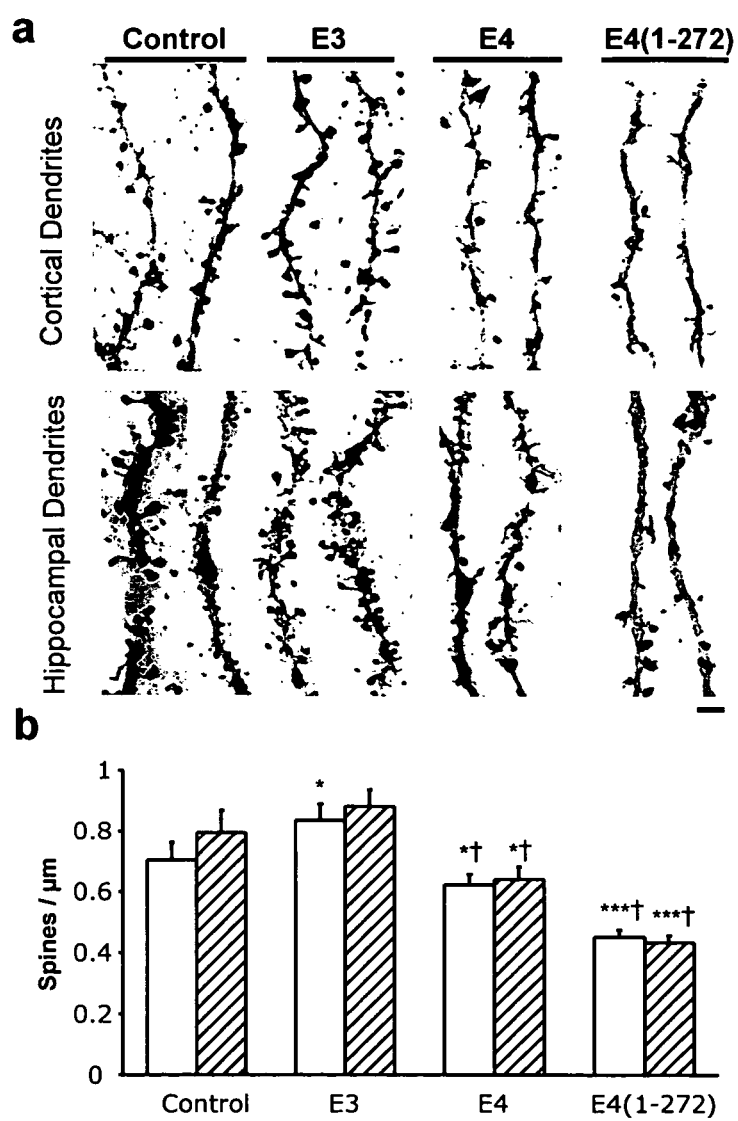
FIGS. 12A and B depict the effect of apoE4 and its fragment on dendritic spine density in rat primary cortical and hippocampal neurons.

To assess the effect of exogenous apoE on dendritic spine density, rat primary cortical and hippocampal neurons, which had been cultured for 14-17 days in vitro, were incubated with different forms of apoE (7.5 µg/ml) for 24 h. Four to six days before the experiment, the cells were transfected with EGFP-tagged β-actin (EGFP-β-actin), a cytoskeletal protein that is abundant in dendritic spines. EGFP-β-actin expression does not impair neuronal function or synaptic morphology (EK751). ApoE3 increased the density of dendritic spines by 20±6% in cortical neurons and by 11±4% in hippocampal neurons, whereas apoE4 caused decreases of 13±5% and 19±5%, respectively, compared with controls; moreover, apoE4 reduced 27±5% and 28±4% compared with apoE3 (FIG. 12). Spinal density was reduced to greatest extent in primary neurons incubated with apoE4(1-272), resulting in a 45±3% reduction versus control and a 55±3% reduction versus apoE3-treated neurons. ApoE4(1-272) significantly reduced the numbers of dendritic branches and branch points as well. Other measures of neuronal complexity (e.g., dendritic field and length of dendritic extensions) were not affected by any form of apoE. These reductions in dendritic spine density suggest that apoE4 and apoE4 fragments impair synaptogenesis or synaptic maintenance. FIGS. 12A and 12B. ApoE4 and its fragment reduce the dendritic spine density in rat primary cortical and hippocampal neurons. (a) Confocal micrographs of synaptic EGFP-β-actin fluorescence in dendrites of rat primary cortical and hippocampal neurons (16 days in vitro) incubated for 24 h with or without (control) various forms of apoE (7.5 µg/ml). Scale bar=5 µm. (b) Number of spines per µm of dendritic extension. Black bars, cortical neurons (20-30 dendrites of 19-23 cells for each condition). White bars, hippocampal neurons (10-15 dendrites of 10-12 cells for each condition). Values are mean±SEM. *P<0.05, ***P<0.001 vs. corresponding control; †P<0.001 vs. corresponding E3 (t test). ApoE4 and its fragment impair mitochondrial dynamics in PC12 cells Synaptogenesis requires normal mitochondrial dynamics and function, and apoE4 and its fragments cause mitochondrial dysfunction. It was determined whether the impairment of synaptogenesis caused by apoE4 and its fragments is associated with impaired mitochondrial dynamics. Highly differentiated neurons have extensive dendritic fields; therefore, synaptic density and activity-dependent synaptogenesis are critically dependent on the appropriate distribution and function of mitochondria in dendritic extensions. Mitochondria are dynamic organelles that are generated around the nucleus and transported by the molecular motor kinesin toward neuronal extensions. To quantify their movement, a microscopic approach was established for fluorescence time-lapse recording of mitochondrial dynamics in neurites of PC12 cells that were differentiated with nervous growth factor (NGF) and transfected with the mitochondrial marker dsRed2-Mito (FIG. 13a-c). During a 15-min recording period, ~23% of the mitochondria were moving (FIG. 13d); the average velocity was 0.67±0.13 µm/min. Neuronal activation by repetitive depolarizations with KCl (4×, 90 mM)$^{42,46}$ reduced the percentage, net distance, and average velocity of moving mitochondria (FIG. 13d-f) but did not affect the speed of movement (moving velocity) (FIG. 13g). Neuronal activation also reduced the mitochondrial index—calculated as added mitochondrial length in a neurite/neurite length—by 22.5%, likely reflecting redistribution toward areas of high energy demand$^{42}$ due to calcium-dependent engagement or disengagement of molecular motors (dynein and kinesin). In contrast, when neuronal activity was inhibited by a 1-h preincubation with tetrodotoxin (TTX, 1 µM), mitochondrial dynamics increased (FIG. 13d-g); the mitochondrial index was not affected. Similar mitochondrial dynamics have been reported in primary neurons.

FIGS. 13A-G. Activity-dependent changes in mitochondrial dynamics in neurites of differentiated PC12 cells. Phase-contrast micrographs of undifferentiated PC12 cells (a) and PC12 cells differentiated for 10 days with NGF (40 ng/ml) (b). (c) Micrograph of dsRed2-Mito fluorescence of (b) (inverted signal), representing mitochondria. (d) Percentage of motile mitochondria under various conditions during a 15-min recording. (e) Net moving distance of mitochondria [(anterograde distance-retrograde distance)/n] during a 15-min recording. (f) Anterograde average velocity (anterograde distance moved/15 min). (g) Anterograde moving velocity (anterograde distance moved/time of moving). In d-g, 198 mitochondria from 14 cells and 126 mitochondria from eight cells in two independent experiments were analyzed for control and KCl depolarization, respectively; 138 mitochondria from four cells in one experiment were analyzed for TTX treatment (1 µM, 1 h preincubation). Values are mean+SEM. *P<0.05, ***P<0.001 vs. control (t test).

Figure 14:
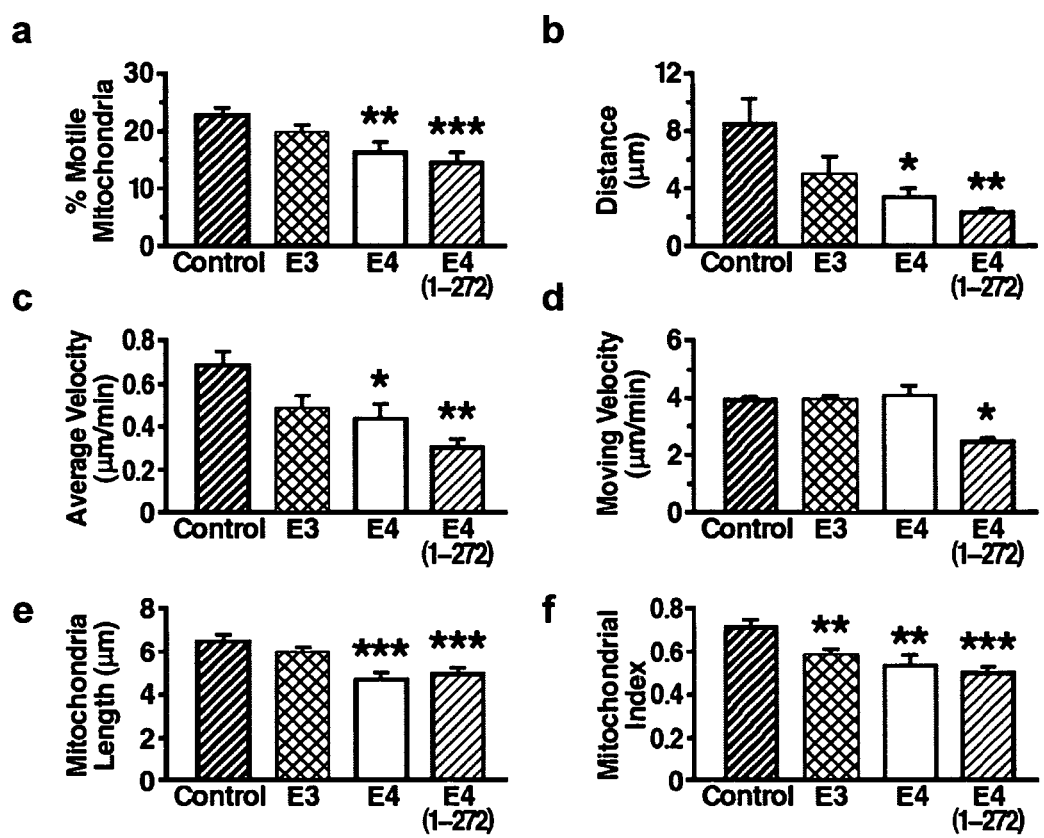
FIGS. 14A-F depict the effect of apoE4 and its fragment on mitochondrial motility and morphology.

Next, the effect of exogenous apoE was assessed by incubating differentiated, dsRed2-Mito-transfected PC12 cells with various forms of apoE (7.5 µg/ml, similar to the level in CSF) for 24 h. The percentage of motile mitochondria was 28±7% lower in apoE4-treated cells than in controls and 37±5% lower in cells treated with apoE4(1-272) (FIG. 14a). The net moving distance was reduced 60±7% by apoE4 and 73±4% by apoE4(1-272) (FIG. 14b). Average anterograde velocity was reduced by 37±10% (apoE4) and 57±6% (fragment) (FIG. 14c); retrograde velocity was unaffected (not shown). Interestingly, only apoE4(1-272) reduced the moving velocity (by 13±3%) (FIG. 3d). ApoE3 did not alter mitochondrial dynamics significantly (FIG. 14a-d). Furthermore, both apoE4 and apoE4(1-272) reduced the average length of mitochondria, while apoE3 did not (FIG. 14e). Finally, all three forms of apoE decreased the mitochondrial index [apoE4(1-272)>apoE4>apoE3] (FIG. 4f).

FIGS. 14A-F. ApoE4 and its fragment reduce mitochondrial motility (a-d) and altered mitochondrial morphology (e-f). Differentiated PC12 cells were incubated for 24 h at 37° C. with or without (control) various forms of apoE (7.5 µg/ml). Mitochondrial dynamics were analyzed as the percentage of moving mitochondria (a), net distance traveled in 15 min (b), average anterograde velocity (c), anterograde moving velocity (d), average mitochondrial length (e), and mitochondrial index (f). Data in a-f are from two independent experiments. In a-d, control: n=198 from 14 cells; apoE3: n=159 from nine cells; apoE4: n=52 from four cells; and apoE4(1-272): n=101 from six cells. In e-f, control: n=229 from 10 cells; apoE3: n=326 from 10 cells; apoE4: n=214 from 6 cells, and apoE4(1-272): n=304 from 11 cells. Values are mean±SEM. *P<0.05, P<0.01, *P<0.001 vs. control; †P<0.05 vs. corresponding E3 (t test).

Figure 15:
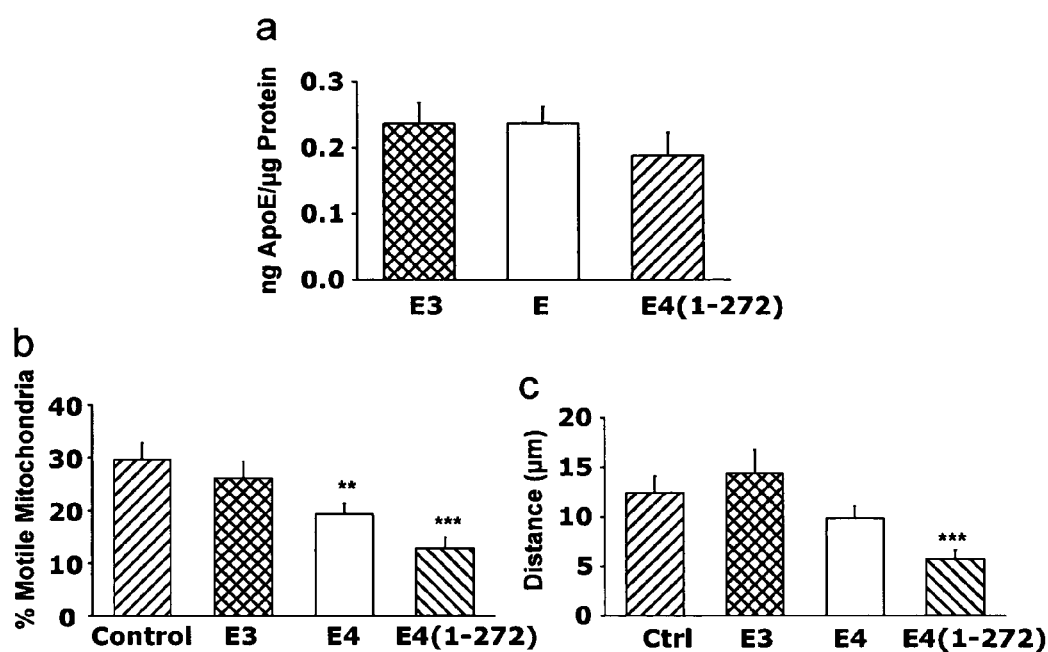
FIGS. 15A-C depict the effect of endogenous apoE4 and its fragment on mitochondrial dynamics in PC12 cells stably expressing various forms of apoE.

Neurons also express apoE under diverse pathophysiological conditions, and neuronal apoE4 undergoes proteolytic cleavage to generate neurotoxic fragments. Therefore, the effects of endogenous apoE on mitochondrial dynamics in differentiated PC12 cells stably expressing low levels of various forms of apoE (~200 pg apoE per µg cellular protein) was determined (FIG. 15a). The percentage of motile mitochondria was reduced 35±7% by apoE4 and 57±8% by apoE4(1-272) but was unaffected by apoE3 (FIG. 15b,c). Thus, endogenous apoE4 and its fragment impaired mitochonodrial dynamics to an even greater extent than when these forms of apoE were applied exogenously.

FIGS. 15A-C. Endogenous apoE4 and its fragment impair mitochondrial dynamics in PC12 cells stably expressing various forms of apoE. PC12 cells stably expressing various forms of apoE at comparable levels (a) were differentiated with NGF (40 ng/ml) for 10 days and then transfected with the dsRed2-Mito construct. Mitochondrial dynamics were analyzed as the percentage of moving mitochondria (b) and net distance traveled in 15 min (c). Control: n=31 from four cells; apoE3: n=26 from four cells; apoE4: n=22 from four cells; and apoE4(1-272): n=21 from four cells. Values are mean±SEM. P<0.01, *P<0.001 vs. control (differentiated untransfected PC12 cells); †P<0.001 vs. corresponding E3 (t test).

ApoE4 and its Fragment do not Impair Mitochondrial Dynamics by Increasing Calcium Influx through Voltage Gated Calcium Channels or NMDA Receptors Repetitive KCl depolarizations alter mitochondrial dynamics by triggering calcium influx due to activation of L-type voltage-sensitive calcium channel (L-VSCCs) and NMDA receptors[42]. To determine if enhanced calcium influx is responsible for the deleterious effects of apoE4 and apoE4 (1-272) on mitochondrial dynamics, differentiated PC12 cells were incubated for 24 h with different forms of apoE and the L-VSCC antagonist nimodipine (5 μM) and the NMDA receptor antagonist 2-amino-5-phosphonovalerate (AP5, 50 μM). Although mitochondrial motility generally increased by about 30% in cells treated with both antagonists, differences in the effects of the different forms of apoE remained significant (FIG. 16).

Figure 16:
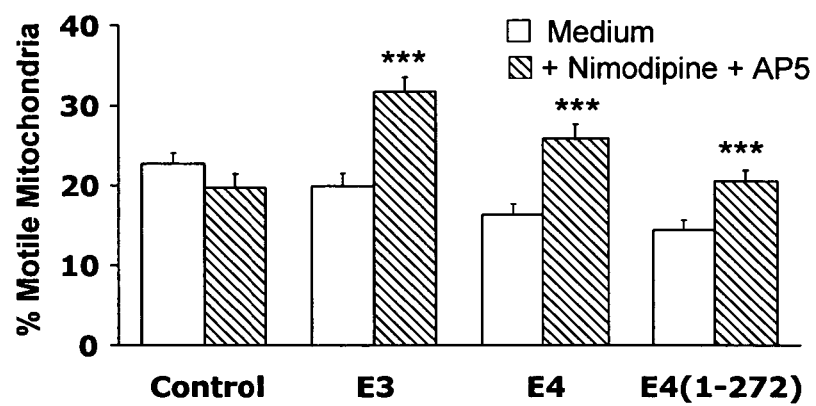
FIG. 16 depicts the effect of blocking calcium influx on apoE-induced impairment of mitochondrial motility.

FIG. 16. Blocking calcium influx does not affect impairment of mitochondrial motility. Differentiated PC12 cells were incubated with or without (control) various forms of apoE (7.5 μg/ml) for 24 h at 37° C. in the absence (open bars) or presence (hatched bars) of the L-type calcium channel blocker nimodipine (5 μM) and the NMDA receptor antagonist AP5 (50 μM) (hatched bars). Mitochondrial motility was analyzed as percentage of moving mitochondria during a 15-min recording. Control: n=61 from five cells; apoE3: n=71 from four cells; apoE4: n=46 from four cells; and apoE4(1-272): n=56 from five cells. Values are mean±SEM. $P<0.01$, *$P<0.001$ vs. corresponding control; $^{\dagger}P<0.05$ vs. the corresponding E3; $^{\dagger\dagger\dagger}P<0.001$ vs. the corresponding E3 (t test).

ApoE4 and its Fragment Impair Mitochondrial Motility in Response to Neuronal Activation Since mitochondrial motility was attenuated by both exogenous and endogenous apoE4 and apoE4(1-272), which is similar to the effect of neuronal activation (FIG. 13d-f), it was hypothesized that continuous "neuronal activation" by apoE4 (1-272) and, to a lesser extent, by full-length apoE4 impairs the responsiveness of mitochondria to further neuronal stimulation. Failure to respond to neuronal stimulation reduces synaptogenesis, leading to learning and memory deficits. To test this hypothesis, differentiated PC12 cells were treated with different forms of apoE (7.5 μg/ml) for 24 h and assessed the mitochondrial response to neuronal activation induced by repetitive depolarizations with KCl. After treatment with apoE3, the percentage of motile mitochondria in response to neuronal activation was reduced by 58±6% (FIG. 17a). However, the extent of this response was reduced to 30% after treatment with apoE4 and was nearly abolished by apoE4(1-272) (FIG. 17a).

ApoE4 and its Fragment Impair Activity-Dependent Synaptogenesis

Figure 13:
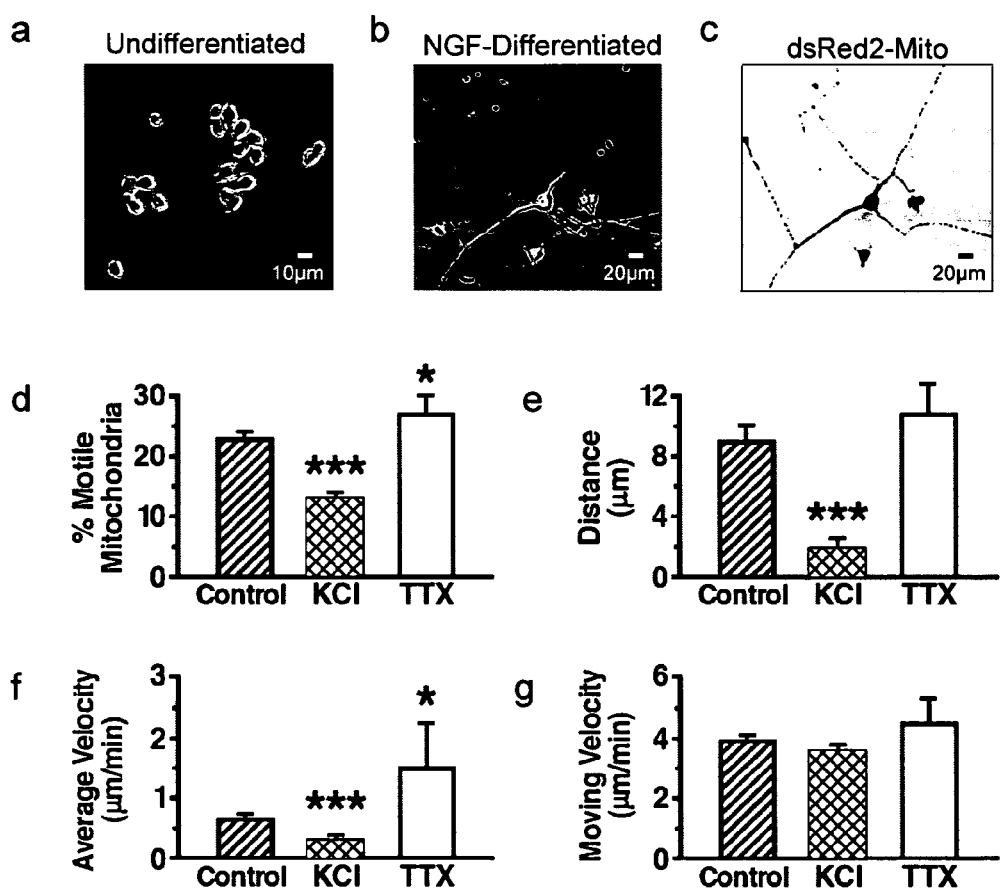
FIGS. 13A-G depict activity-dependent changes in mitochondrial dynamics in neurites of differentiated PC12 cells.

In similar experiments with primary cortical neurons, dendritic spine density was quantified to assess effects on activity-dependent synaptogenesis. In response to neuronal activation, spinal density was reduced 48±11% by apoE4 and 49±10% by apoE4(1-272) as compared to controls (FIG. 17b). These reductions were comparable to those in neurons treated with apoE4 and its fragment in the absence of neuronal activation (FIG. 13).

FIGS. 17A and 17B. ApoE4 and its fragment impair the activity-dependent mitochondrial dynamics and synaptogenesis. (a) Differentiated PC12 cells were incubated for 24 h at 37° C. with or without (control) various forms of apoE (7.5 μg/ml, open bars). After incubation, some cells were repetitively depolarized with 90 mM KCl (four times for 3 min each, separated by 10-min washes) (closed bars), and mitochondrial dynamics were analyzed. For nondepolarization, control: n=198 from 14 cells; apoE3: n=159 from nine cells; apoE4: n=52 from four cells; and apoE4(1-272): n=101 from six cells. For KCl depolarization, control: n=48 from four cells; apoE3: n=31 from four cells; apoE4: n=26 from three cells; and apoE4(1-272): n=40 from five cells. (b) Primary cortical neurons were incubated with or without (control) various forms of apoE (7.5 μg/ml) for 24 h and repetitively depolarized as in a, and the number of spines per μm of dendritic extension was analyzed (10-15 dendrites of 10-15 cells for each condition). Values are mean±SEM. *$P<0.001$ vs. no-depolarized condition in (a) and $P<0.01$ vs. control or E3 in (b) (t test).

Neuronal Inhibition Rescues Deficits in Mitochondrial Dynamics and Synaptogenesis Induced by apoE4 and its Fragment To further test whether the deficits in mitochondrial dynamics and synaptogenesis are dependent on neuronal activity, we incubated primary neurons for 24 h with various forms of apoE and TTX, which inhibits neuronal activity. No significant differences in mitochondrial dynamics (FIG. 18a) or dendritic spine density (FIG. 18b) were observed.

Figure 18:
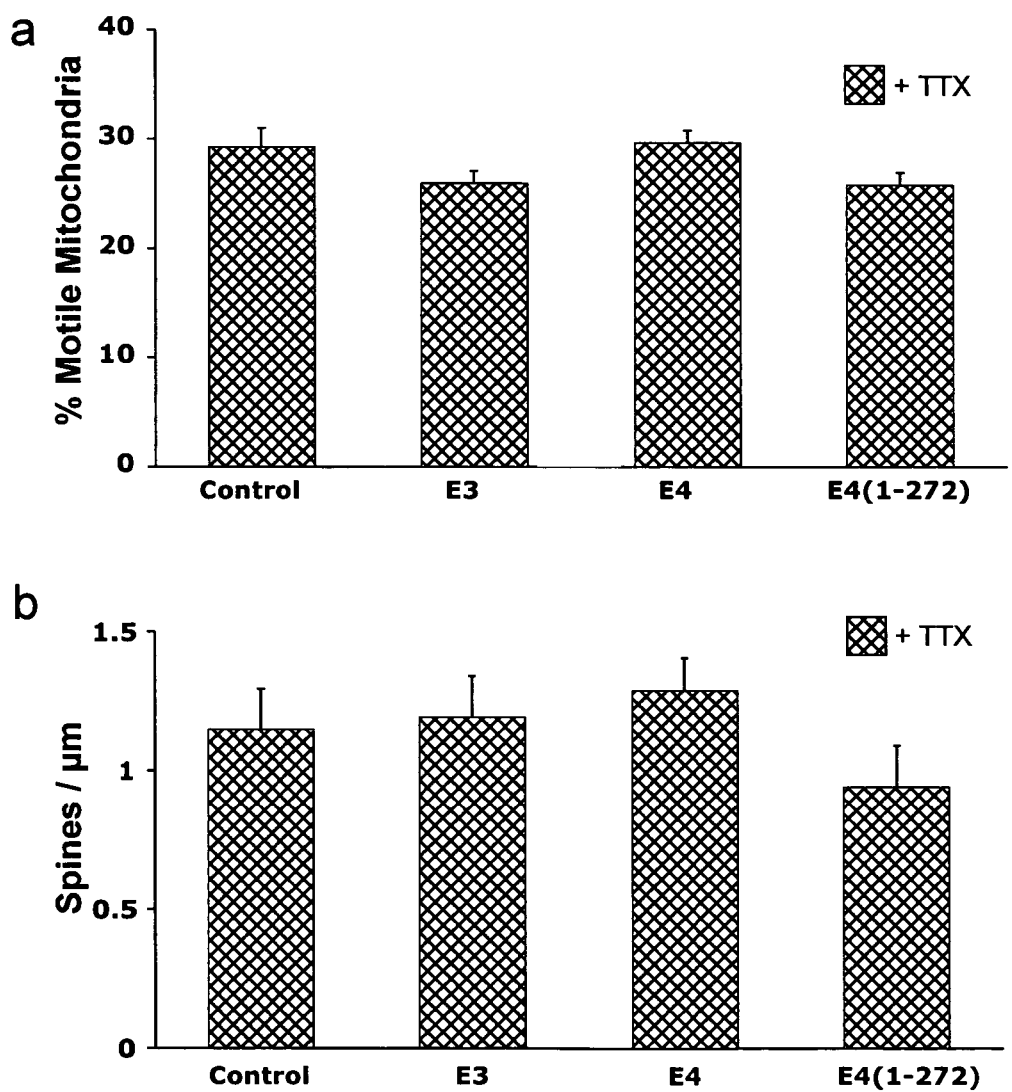
FIGS. 18A and 18B depict the effect of neuronal inhibition on deficits in mitochondrial dynamics and synaptogenesis.

FIGS. 18A and 18B. Neuronal inhibition rescues deficits in mitochondrial dynamics and synaptogenesis. (a) Differentiated PC12 cells were incubated with or without (control) various forms of apoE (7.5 μg/ml) for 24 h at 37° C. in the presence of 1 μM TTX. Mitochondrial dynamics was analyzed as percentage of moving mitochondria. Control: n=45 from 4 cells; apoE3: n=42 from 6 cells; apoE4: n=32 from 7 cells; apoE4(1-272): n=87 from 8 cells. (b) Cortical primar were incubated with various forms of apoE (7.5 μg/ml) for 24 h in the presence of 1 μM TTX. The numbers of spines per μm dendritic extension were analyzed (10-12 dendrites of 10-11 cells for each condition). Values are mean±SEM.

ApoE4 and its Fragment Reduce the Number, Size, and Distribution of Mitochondria in Dendrites of Primary Neurons Since activity-dependent synaptogenesis and synaptic function require appropriate mitochondrial localization, the number and distribution of mitochondria in dendritic extensions in response to treatment with various forms of apoE were analyzed. Dendritic spines had many fewer mitochondria in apoE4-treated cells than in apoE3-treated cells or controls, and even fewer in cells treated with apoE4(1-272). To quantify the distribution of mitochondrial distribution, the area occupied by mitochondria per micrometer of dendritic extension was calculated. This area was 25±6% smaller in apoE4-treated than apoE3-treated cells (FIG. 19A). The reduction was even greater (44±9%) in cells treated with apoE4(1-272). In addition, apoE4(1-272) reduced the average size of dendritic mitochondria by 25% as compared to apoE3 and apoE4 (FIG. 19B), suggesting that apoE4 fragment stimulates mitochondrial fission or causes mitochondrial fragmentation.

FIGS. 19A and 19B. ApoE4 and its fragment reduce the occupancy of mitochondria in dendrites of primary cortical neurons. Mitochondrial occupancy (area occupied by mitochondria per μm dendritic extension) (a) and size distribution of mitochondria (b) in dendrites of six cells per condition. Values in (a) are mean±SEM. $P<0.01$, *$P<0.001$ vs. E3 (t test). (c) The distribution of mitochondrial sizes (Mito-size) in cells treated with apoE4(1-272) differed significantly from that in cells treated with apoE3 or apoE4 ($P<0.05$, linear regression analysis, Pearson correlation coefficient).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of identifying an agent that reduces neurotoxic apolipoprotein E4 (apoE4) induced impairment of mitochondria, the method comprising:
   contacting a neuronal cell with a test agent, wherein the neuronal cell has been genetically modified with an expression vector that comprises a nucleotide sequence encoding a toxic apoE4 polypeptide comprising an amino acid sequence having at least 95% amino acid sequence identity to amino acids 1-272 of the amino acid sequence set forth in SEQ ID NO:1 and lacking amino acids 273-299 of the amino acid sequence set forth in SEQ ID NO:1,
   wherein said nucleotide sequence is operably linked to a promoter functional in a neuronal cell, and wherein the neuronal cell comprises in a mitochondrion a fluorescent polypeptide or a fluorescent dye that provides for visualization of the mitochondrion; and
   determining the effect, if any, of the test agent on one or more of the number of mitochondria in a dendrite, the size of mitochondria, the membrane potential of mitochondria, and mitochondrial motility, and wherein an increase in the number of mitochondria in a dendrite, the size of mitochondria, the membrane potential of mitochondria, or mitochondrial motility, indicates that the test agent reduces neurotoxic apoE4-induced impairment of mitochondria.

2. The method of claim 1, wherein the toxic apoE4 polypeptide is a fusion protein comprising an apoE polypeptide and a fusion partner that provides for detection or ease of purification of the apoE4 polypeptide.

3. The method of claim 2, wherein the fusion partner is a green fluorescent protein.

4. The method of claim 1, wherein the fluorescent polypeptide comprises a mitochondrial localization signal.

5. The method of claim 4, wherein the mitochondrial localization signal is a mitochondrial localization signal of cytomegalovirus protein pUL37$_S$, a mitochondrial localization signal of yUng1p, a pseudorabies virus serine/threonine kinase Us3 mitochondrial localization signal, or a peptide comprising the amino acid sequence set forth in SEQ ID NO:25.

6. The method of claim 1, wherein the neuronal cell is a cell of an established neuronal cell line or a primary neuron.

7. The method of claim 1, wherein the fluorescent protein is a red fluorescent protein.

8. The method of claim 1, wherein the promoter is a neuron-specific enolase promoter, a neurofilament gene promoter, a synaptophysin promoter, a tyrosine hydroxylase promoter, an aromatic amino acid decarboxylase promoter, a synapsin promoter, a serotonin receptor promoter, or an enkephalin promoter.

9. A method of identifying an agent that reduces neurotoxic apolipoprotein E4 (apoE4)-induced impairment of mitochondria, the method comprising:
  contacting a neuronal cell with a test agent, wherein the neuronal cell has been genetically modified with an expression vector that comprises a nucleotide sequence encoding a toxic apoE polypeptide comprising an amino acid sequence having at least 95% amino acid sequence identity to the amino acid sequence set forth in SEQ ID NO:1 and having a mutation of one or more of L279, K282, and Q284, relative to SEQ ID NO:1, such that the apoE4 is neurotoxic,
  wherein said nucleotide sequence is operably linked to a promoter functional in a neuronal cell, and wherein the neuronal cell comprises in a mitochondrion a fluorescent polypeptide or a fluorescent dye that provides for visualization of the mitochondrion; and
  determining the effect, if any, of the test agent on one or more of the number of mitochondria in a dendrite, the size of mitochondria, the membrane potential of mitochondria, and mitochondrial motility, and wherein an increase in the number of mitochondria in a dendrite, the size of mitochondria, the membrane potential of mitochondria, or mitochondrial motility, indicates that the test agent reduces neurotoxic apoE4-induced impairment of mitochondria.

10. The method of claim 9, wherein the neurotoxic apoE4 polypeptide comprises one or more of an L279Q mutation, a K282A mutation, and a Q284A mutation.

11. The method of claim 9, wherein the toxic apoE4 polypeptide is a fusion protein comprising an apoE polypeptide and a fusion partner that provides for detection or ease of purification of the apoE4 polypeptide.

12. The method of claim 11, wherein the fusion partner is a green fluorescent protein.

13. The method of claim 9, wherein the fluorescent polypeptide comprises a mitochondrial localization signal.

14. The method of claim 13, wherein the mitochondrial localization signal is a mitochondrial localization signal of cytomegalovirus protein pUL37$_S$, a mitochondrial localization signal of yUng1p, a pseudorabies virus serine/threonine kinase Us3 mitochondrial localization signal, or a peptide comprising the amino acid sequence set forth in SEQ ID NO:25.

15. The method of claim 9, wherein the neuronal cell is a cell of an established neuronal cell line or a primary neuron.

16. The method of claim 9, wherein the fluorescent protein is a red fluorescent protein.

17. The method of claim 9, wherein the promoter is a neuron-specific enolase promoter, a neurofilament gene promoter, a synaptophysin promoter, a tyrosine hydroxylase promoter, an aromatic amino acid decarboxylase promoter, a synapsin promoter, a serotonin receptor promoter, or an enkephalin promoter.

* * * * *